(12) United States Patent
Kaji

(10) Patent No.: US 11,660,505 B2
(45) Date of Patent: May 30, 2023

(54) STABILITY EVALUATION SYSTEM, PROGRAM, AND METHOD

(71) Applicant: LEOMO, Inc., Boulder, CO (US)

(72) Inventor: Kunihiko Kaji, Tokyo (JP)

(73) Assignee: LEOMO, Inc., Boulder, CO (US)

( * ) Notice: Subject to any disclaimer, the term of this patent is extended or adjusted under 35 U.S.C. 154(b) by 0 days.

(21) Appl. No.: 17/917,556

(22) PCT Filed: Apr. 7, 2021

(86) PCT No.: PCT/JP2021/014732
§ 371 (c)(1),
(2) Date: Oct. 7, 2022

(87) PCT Pub. No.: WO2021/210461
PCT Pub. Date: Oct. 21, 2021

(65) Prior Publication Data
US 2023/0123441 A1 Apr. 20, 2023

(30) Foreign Application Priority Data
Apr. 13, 2020 (JP) ............................. JP2020-071816

(51) Int. Cl.
*A63B 24/00* (2006.01)
*G01P 13/00* (2006.01)
*A63B 71/06* (2006.01)

(52) U.S. Cl.
CPC .......... *A63B 24/0062* (2013.01); *G01P 13/00* (2013.01); *A63B 2024/0068* (2013.01);
(Continued)

(58) Field of Classification Search
CPC .............. A63B 24/0062; A63B 4/0068; A63B 2071/0652; A63B 2220/803;
(Continued)

(56) References Cited

U.S. PATENT DOCUMENTS

| | | | |
|---|---|---|---|
| 7,031,872 B2* | 4/2006 | Tanaka .................. | A61B 5/4023 324/160 |
| 2011/0009777 A1 | 1/2011 | Reichow et al. | |
| 2013/0316855 A1 | 11/2013 | Mace | |
| 2014/0228989 A1 | 8/2014 | Tagliabue | |
| 2015/0317515 A1 | 11/2015 | Lake, II et al. | |
| 2018/0021628 A1 | 1/2018 | Lee et al. | |
| 2018/0264320 A1* | 9/2018 | Chang ................... | A61B 5/1118 |

(Continued)

FOREIGN PATENT DOCUMENTS

| | | | | | |
|---|---|---|---|---|---|
| CN | 105979859 A | * | 9/2016 | ............... | A61B 5/00 |
| CN | 106859616 A | * | 6/2017 | ......... | A61B 5/02055 |

(Continued)

OTHER PUBLICATIONS

International Search Report for PCT/JP2021/014732 dated Jun. 29, 2021.
PCT written opinion dated Jun. 29, 2021.

*Primary Examiner* — Octavia Davis Hollington
(74) *Attorney, Agent, or Firm* — Yokoi & Co., U.S.A.; Toshiyuki Yokoi

(57) ABSTRACT

A stabilizing ability, so-called stability, according to a change in body motion of a wearer is to be appropriately evaluated to achieve effective training, coaching, and fitting of athletic equipment.
Provided are a plurality of body motion sensors 40 that is attached to a wearer 1 or an arbitrary part of a barbell 1a to be used by the wearer 1 and is capable of detecting three-dimensional displacement or rotation of each part, a memory that records a detection result by the plurality of body motion sensors 40 as body motion data and stores index data holding a correlation between an amount of deviation from a stable reference value for evaluating reproducibility of body motion and an index for evaluating a stabilizing ability, an index calculation unit 117g that refers to the index data based on a reference value or a threshold acquired from the (Continued)

recorded body motion data and calculates the index for evaluating the stabilizing ability, and an output device that displays or outputs the index calculated by the index calculation unit 117g.

18 Claims, 8 Drawing Sheets

(52) U.S. Cl.
CPC .............. *A63B 2071/0652* (2013.01); *A63B 2220/803* (2013.01); *A63B 2220/836* (2013.01); *A63B 2225/02* (2013.01); *A63B 2225/50* (2013.01)

(58) Field of Classification Search
CPC .............. A63B 2220/836; A63B 25/02; A63B 2225/50; G01P 13/00; A61B 5/6898; A61B 5/6807; A61B 5/02108; G16H 40/63

See application file for complete search history.

(56) References Cited

U.S. PATENT DOCUMENTS

| | | | |
|---|---|---|---|
| 2019/0275372 A1 | 9/2019 | Kaji et al. | |
| 2020/0146592 A1 | 5/2020 | Tsukada et al. | |
| 2022/0005575 A1* | 1/2022 | Ueda | G16H 40/63 |
| 2023/0073679 A1* | 3/2023 | Paszicsnyek | G16H 40/63 |

FOREIGN PATENT DOCUMENTS

| | | | | | |
|---|---|---|---|---|---|
| JP | WO2002043586 A1 | * | 4/2004 | | |
| JP | 2012213624 A | * | 11/2012 | | |
| JP | 2012-532695 A | | 12/2012 | | |
| JP | 2013-215590 A | | 10/2013 | | |
| JP | 2013-244405 A | | 12/2013 | | |
| JP | 2016-524929 A | | 8/2016 | | |
| JP | 2017018603 A | * | 1/2017 | ............. | A41D 1/002 |
| JP | 2020-880 A | | 1/2020 | | |
| KR | 10-2017-0123089 A | | 11/2017 | | |
| KR | 10-2031243 B | | 10/2019 | | |
| WO | 2018/100696 A | | 6/2018 | | |
| WO | 2019/035444 A | | 2/2019 | | |

* cited by examiner

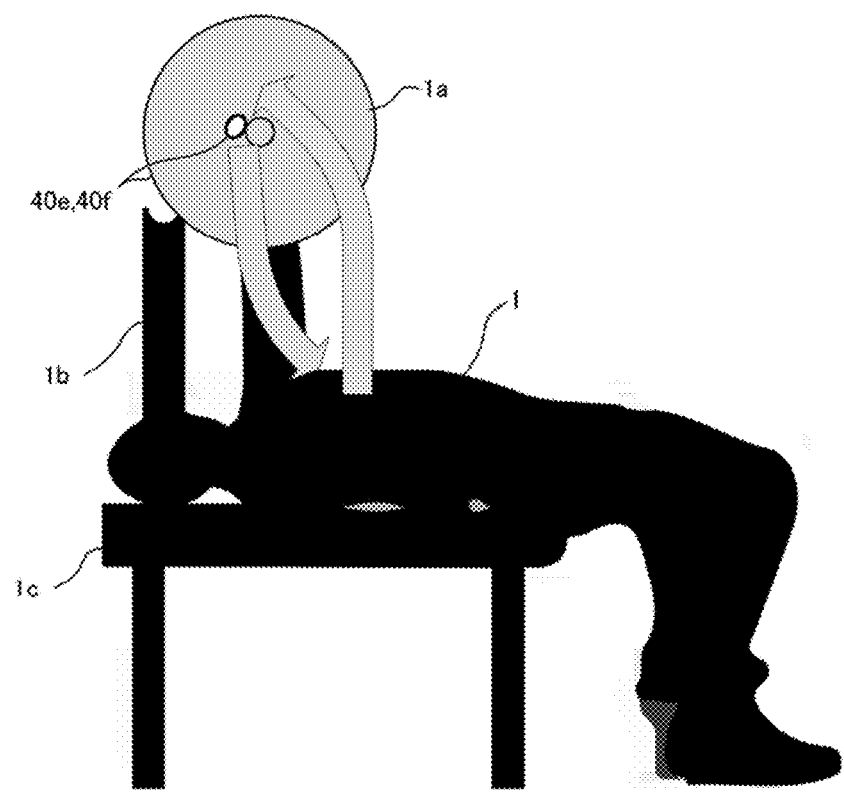

STABILITY EVALUATION SYSTEM, PROGRAM, AND METHOD

TECHNICAL FIELD

The present invention relates to a stability evaluation system, a program, and a method that detect body motion of a wearer and evaluate a stabilizing ability according to a change in the body motion, using a so-called smartphone, wearable type, or other information terminal devices.

BACKGROUND ART

In recent years, information terminal devices have become smaller, lighter, and more multifunctional, and wearable information processing terminals so-called wearable terminals that can be attached to the body of a user are becoming widespread. Since such wearable terminals are lightweight and have a communication function with various sensors such as a heart rate sensor, in addition to a clock function and a GPS function, a system has been developed to record, monitor, and evaluate body motion by attaching the wearable terminals during sports training such as running, walking, and bicycle racing, exercising, and fitting (for example, Patent Literature 1).

According to the system disclosed in Patent Literature 1, by attaching a device that measures exercising parameters to a user, comparing the exercising parameters obtained by monitoring the exercising user during the exercise activity with basic baseline data, and changing music to be played or the like according to whether the comparison result is within an allowable range, it is possible to provide feedback to the user in real time during the exercise activity.

PRIOR ART DOCUMENTS

Patent Documents

Patent Document 1: JP 2013-215590 A

SUMMARY OF THE INVENTION

Problems to be Solved by the Invention

However, in the technique disclosed in the above Patent Literature, since it is only determined whether the motion range of the form of the user who is currently exercising is within the allowable range by comparing the exercising parameters obtained by monitoring the exercising user with basic baseline data, there are many cases where the user is in a good form but cannot maintain the form for a long time, and appropriate training and coaching have not been achieved.

Therefore, the present invention is to solve the above problems, and a purpose of the present invention is to provide a stability evaluation system, a program, and a method that appropriately evaluate a stabilizing ability, so-called stability, according to a change in body motion of a wearer to achieve effective training, coaching, and fitting of athletic equipment.

Means for Solving Problem

In order to solve the above problems, the present invention is a stability evaluation system configured to detect body motion of a wearer and evaluate a stabilizing ability according to a change in the body motion, the system including a plurality of body motion sensors that is attached to the wearer or an arbitrary part of equipment to be used by the wearer and is capable of detecting three-dimensional displacement or rotation of each part, a body motion recording unit configured to record a detection result by the plurality of body motion sensors as body motion data, a storage unit configured to store index data holding a correlation between an amount of deviation from a stable reference value for evaluating reproducibility of the body motion and an index for evaluating the stabilizing ability, an index calculation unit configured to refer to the index data based on a reference value or a threshold acquired from the body motion data recorded in the body motion recording unit and calculate the index for evaluating the stabilizing ability, and an output device configured to display or output the index calculated by the index calculation unit.

The present invention is a stability evaluation method to detect body motion of a wearer and evaluate a stabilizing ability according to a change in the body motion, the method including:

(1) a body motion recording step of measuring, by a plurality of body motion sensors attached to the wearer or an arbitrary part of equipment to be used by the wearer, three-dimensional displacement or rotation of each part, and recording a detection result by the plurality of body motion sensors as body motion data in a body motion recording unit;

(2) an index calculation step of referring to index data holding a correlation between an amount of deviation from a stable reference value for evaluating reproducibility of body motion and an index for evaluating the stabilizing ability, and calculating, by an index calculation unit, the index for evaluating the stabilizing ability based on a reference value or a threshold acquired from the body motion data recorded in the body motion recording unit; and (3) an output step of displaying or outputting, by an output device, the index calculated in the index calculation step.

In the above invention, it is preferable to further includes:

a parameter presentation step, by a parameter setting unit, of extracting a parameter related to a load applied to the wearer or an arbitrary part of equipment to be used by the wearer based on the body motion data detected by the plurality of body motion sensors, acquiring, among extracted parameters, a setting value of a parameter for applying a certain load as a setting parameter, and presenting the acquired setting parameter to the wearer;

a load determination step of monitoring the setting parameter presented by the parameter presentation unit and determining, by a load determination unit, whether the specific load is applied; and a reference value setting step of setting, by a reference value setting unit, the reference value based on body motion data related to the setting parameter in a state where the load determination unit determines that the specific load is applied, in which the index calculation unit refers to the index data based on the reference value or the threshold set by the reference value setting unit to calculate the index for evaluating the stabilizing ability in the index calculation step.

Furthermore, in the above invention, it is preferable to further includes a stability calculation step of calculating, by a stability calculation unit, a stable period during which a stable state of the body motion is continued, based on an amount of deviation from the acquired reference value, wherein the storage unit stores, as the index data, a correlation between the stabilization period calculated by the stability calculation unit, the amount of deviation after the stabilization period, and the index for evaluating the stabilizing ability, and the index calculation unit refers to the index data according to a calculation result of the stability calculation unit to calculate the index for evaluating the stabilizing ability in the index calculation step.

In the above invention, it is preferable that the index calculation unit sets, as the reference value, a value selected from an average value, a maximum value, a minimum value, or an arbitrary representative value within the predetermined period based on a setting operation by an operator. In the above invention, it is further preferable that the index data holds a correlation of the body motion of the wearer related to the bicycle movement during riding of a bicycle, the setting of the bicycle, the traveling speed or the traveling distance in bicycle racing, the input power transmitted to the wheels (or pedals), the cadence (rotation speed), and the like. In the above invention, it is further preferable that the index data holds a correlation between the body motion of the wearer during competition (including all behaviors and actions involving body motion such as acting, playing, or training) and an incidence of injuries or failures during the competition.

In the above invention, it is preferable to further include a cycle extraction unit configured to extract cyclical motion of each of the plurality of body motion sensors based on the body motion data recorded in the body-motion recording unit, and a stability calculation unit configured to set, as a stable reference value, a reference value acquired within a predetermined period based on a parameter related to the cyclical motion extracted by the cycle extraction unit and calculate, based on an amount of deviation from the stable reference value, a stable period during which a stable state of the cyclical motion is continued, in which the storage unit stores, as the index data, a correlation between the stable period calculated by the stability calculation unit, the amount of deviation after the stable period, and the index for evaluating the stabilizing ability, and the index calculation unit refers to the index data according to a calculation result by the stability calculation unit and calculates the index for evaluating the stabilizing ability.

Note that the system and method according to the present invention described above can be implemented by executing a program of the present invention described in a predetermined language on a computer. That is, the present invention is a stability evaluation program to detect body motion of a wearer and evaluate a stabilizing ability according to a change in the body motion using a plurality of body motion sensors that is attached to the wearer or an arbitrary part of equipment to be used by the wearer and is capable of detecting three-dimensional displacement or rotation of each part, the stability evaluation program causing an information processing terminal to function as a body-motion recording unit configured to record a detection result by the plurality of body motion sensors as body motion data, a storage unit configured to store index data holding a correlation between an amount of deviation from a stable reference value for evaluating reproducibility of the body motion and an index for evaluating the stabilizing ability, an index calculation unit configured to refer to the index data based on a reference value or a threshold acquired from the body motion data recorded in the body-motion recording unit and calculate the index for evaluating the stabilizing ability, and an output device configured to display or output the index calculated by the index calculation unit.

By installing such a program of the present invention in an IC chip or a memory device of a portable terminal device, a smartphone, a wearable terminal, a tablet PC, other information processing terminals, a general-purpose computer, such as a personal computer or a server computer, and executing the program by the CPU, a system having the above functions can be constructed, and the method according to the present invention can be performed.

Effects of the Invention

As described above, according to the present invention, it is possible to appropriately evaluate body motion of a wearer using a correlation between a stabilizing ability according to a change in the body motion such as an amount of deviation from a stable reference value for evaluating reproducibility of the body motion of the wearer, so-called stability, and an evaluation index, and to achieve effective training, coaching, and fitting of athletic equipment. Specifically, conventionally, as in conventional weight training, a stable reference value for evaluating the reproducibility of order of the parts that start to move and body motion in repetitive motion such as vertical motions in a state where a load is applied is obtained, and the stabilizing ability is evaluated by an amount of deviation from the stable reference value.

Accordingly, by referring to the index data based on the number of proper body motions and the amount of deviation, it is possible to predict a possibility of occurrence of a failure such as an injury and take measures such as notifying the wearer of an alert in real time. In addition, during bicycle racing or fitting, it is possible to guide the athlete to maintain the form and concentrate on riding until the end of the racing when the athlete is tired after the start of riding and is in an imbalanced form, such as riding in a form that is aerodynamically disadvantageous, in the latter half of the racing, and to notify the athlete of an alert when an injury or failure is likely to occur.

In addition, according to the present embodiment, the length of the stable period during which the reference value, the threshold, and the stable reference value are maintained is detected to evaluate whether the stability of the body motion is secured or the body motion is correctly reproduced. Therefore, by appropriately setting the reference value, the width of the threshold, or the like, it is possible to detect a small change before the form is visibly imbalanced and coach the wearer to make small correction to maintain the stability.

BRIEF DESCRIPTION OF THE DRAWINGS

FIG. 3 is an example of body-motion reproduction data acquired in an embodiment.

MODE FOR CARRYING OUT THE INVENTION

First Embodiment

Hereinafter, a first embodiment of the present invention will be described with reference to the drawings. In the present embodiment, the present invention using an information terminal device 100 is applied to loaded repetitive exercises such as weight training to provide a system that enables body motion measurement and coaching in such training. Note that the embodiment described below exemplifies a device or the like for embodying the technical idea of the present invention, and the technical idea of the present invention does not specify the material, shape, structure, arrangement, and the like of each component to those described below. Various modifications can be made to the technical idea of the present invention within the scope of the claims.

(Configuration of Stability Evaluation System)

Figure 1A:
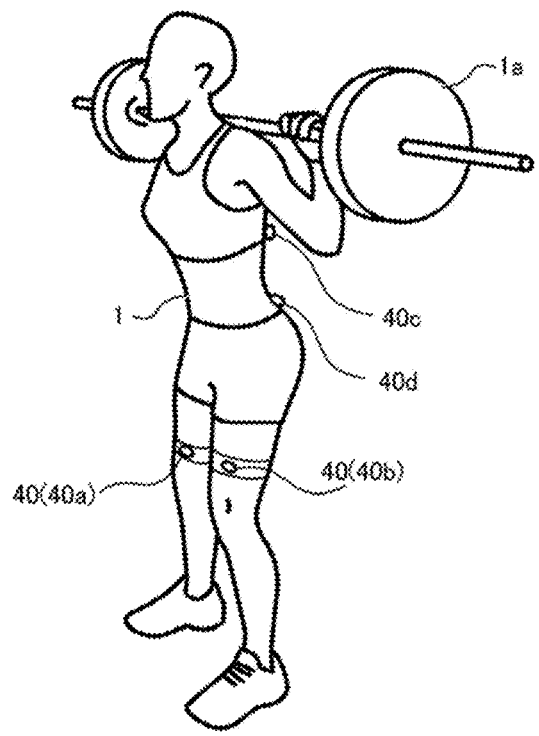
FIGS. 1A and 1B are explanatory diagrams illustrating a usage mode of a stability evaluation system according to an embodiment.
Figure 1B:
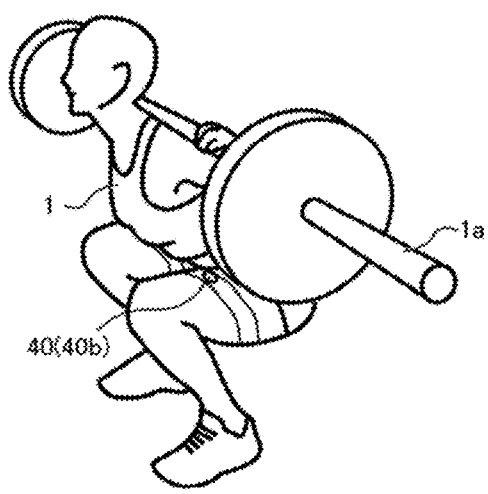
Figure 2A:
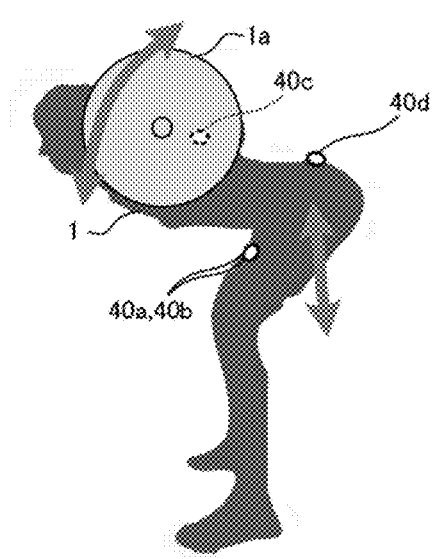
FIGS. 2A and 2B are example of body-motion reproduction data acquired in an embodiment.
Figure 2B:
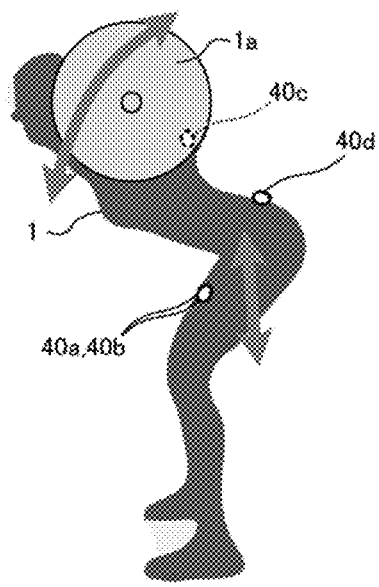
Figure 4A:
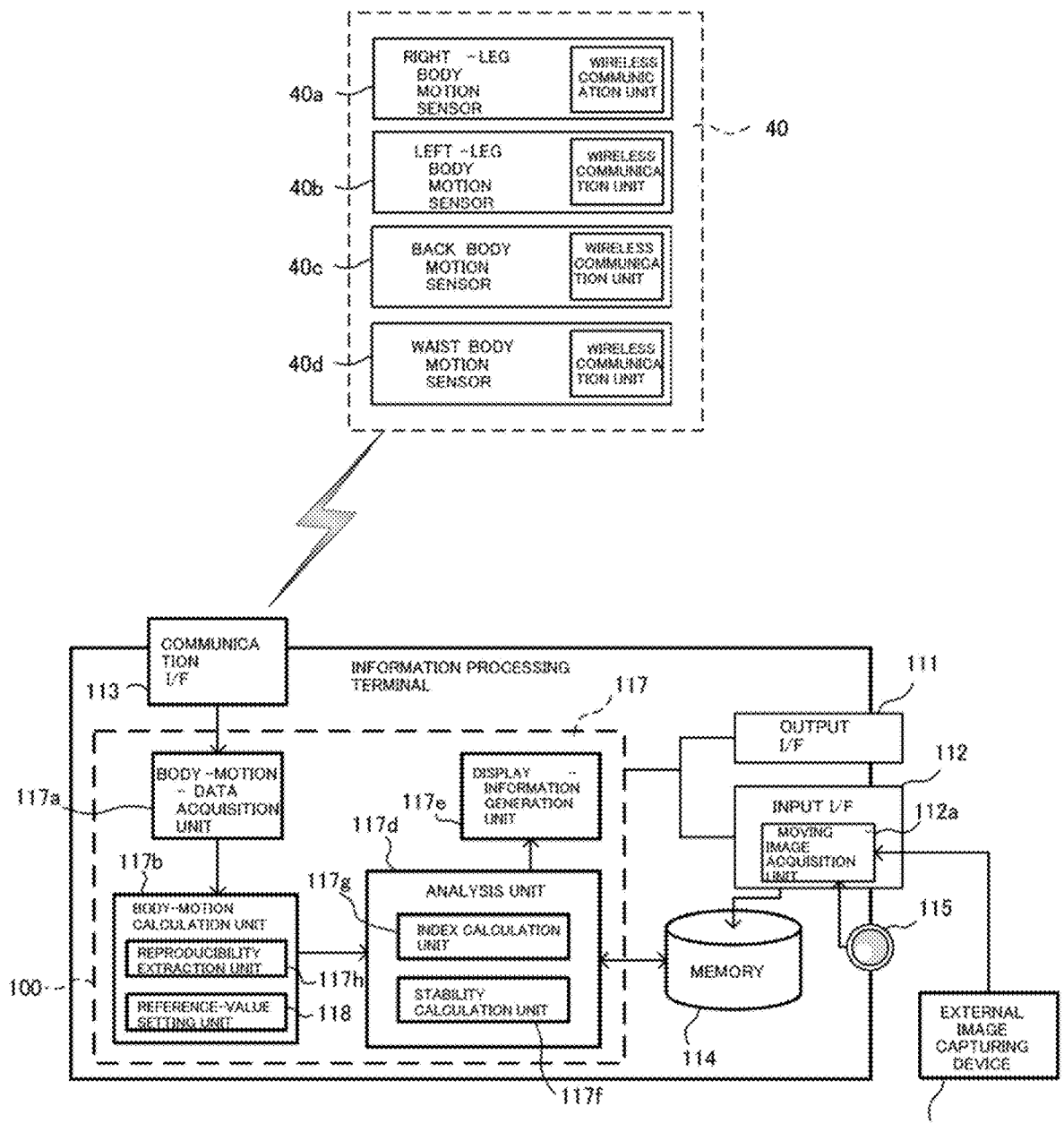
FIGS. 4A and 4B are block diagrams illustrating an internal configuration of each device according to an embodiment.
Figure 4B:
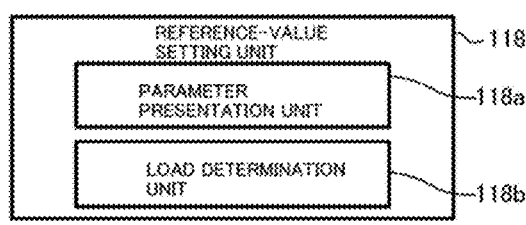

FIGS. 1A and 1B are explanatory diagrams illustrating a usage mode of a stability evaluation system using the information terminal device 100 according to the present embodiment. FIGS. 2A and 2B and 3 are examples of body-motion reproduction data acquired by the stability evaluation system according to the present embodiment. FIGS. 4A and 4B are block diagrams illustrating an internal configuration of each device.

As illustrated in FIGS. 1A to 4B, the stability evaluation system according to the present embodiment includes the information terminal device 100 used by a wearer 1, and body motion sensors 40 (40a to 40d, or 40e and 40f) each attached to a body part of the wearer 1 and wirelessly connected to the information terminal device 100.

Then, in the present system, these body motion sensors 40 are used to set a stable reference value for evaluating the reproducibility of body motion, and an index for evaluating a stabilizing ability based on the amount of deviation from the stable reference value is provided. This index is obtained by referring to index data, and the index data holds, for example, a correlation between body motion of a wearer during competition and an incidence of injuries or failures during the competition, the suitability of equipment to be used, such as a barbell for weight training, and the like. In the present embodiment, the index for evaluating a stabilizing ability is obtained by referring to the index data based on a reference value or a threshold acquired from body motion data. The reference value can be selected from an average value, a maximum value, a minimum value, or an arbitrary representative value within a predetermined period based on a setting operation by the wearer.

In the present embodiment, the index data holds a correlation between body motion of a wearer during weight training and an incidence of injuries or failures during competition or training, and when the motion of the wearer during the training or competition includes something that causes injuries or failures, the wearer is notified of the fact by an alert or the like. For example, in weight training, running, or the like, a stable reference value for repetitive motion is calculated, and the index data is referred to by monitoring deviation from the stable reference value (for example, a difference from the first time in weight training, or the like) to calculate an incidence of injuries or failures according to the amount of deviation. Then, when the possibility of occurrence of injuries or the like increases, an abnormal value is notified to the wearer. At this time, an abnormal value may be eliminated through operation determination processing.

As another method, in the case of weight training, the body motion sensors 40 may be attached to the bar, the back, the waist, and the thighs to evaluate the order of the parts that start to move in repetitive motion such as vertical motions, body motion data for each time, or a difference from the first time. Accordingly, it is possible to detect a case where the wearer is moving from a position different from the original motion as a starting position during weight training or a case where the wearer is moving to make a trigger by rotating the waist during squatting and record, as a result, the number of proper motions and the number of improper motions (the number of large changes, or the like). In particular, since differences in motions of the waist and the back can lead to injuries, such an amount of deviation and an index value are associated on the index data and referred to, in order to notify the wearer of an alert in real time.

(Configuration of Each Device)

In the following, a specific internal configuration of each device constituting the present system is described.

(1) Body Motion Sensor

The body motion sensors 40a to 40d are sensors that are attached to parts of the wearer 1 or equipment, such as the barbell 1a, to be used by the wearer 1 to exercise, and detect three-dimensional displacement or rotation of each part. In the present embodiment, the body motion sensors 40 include right-leg/left-leg body motion sensors 40a and 40b to be attached to the right and left thighs of the wearer, and waist/back body motion sensors 40c and 40d to be attached to the median line of the body such as the waist, the back, the pelvis, and the like of the wearer 1. These body motion sensors 40a to 40d are each equipped with a three-axis accelerometer that measures acceleration of an object, a three-axis gyroscope that detects angular velocity of the object, and a three-axis magnetic sensor that measures the magnitude and direction of a magnetic field, and can detect motion in nine axes. Note that each body motion sensor 40 can be attached to and detached from equipment such as shoes, a belt, clothes, or a barbell of the wearer by a member such as a clip, and each sensor is easily installed to perform measurement, which allows continuous measurement without a burden on the wearer.

As illustrated in FIGS. 4A and 4B, each of the body motion sensors 40 (each of the body motion sensors 40a to 40d) includes a wireless communication unit. The wireless communication unit has an antenna inside, and can perform communication processing with the information terminal device 100 by a function of executing a data communication protocol for near field communication by Bluetooth (registered trademark) Low Energy (BTLE), Bluetooth (registered trademark) 4.0, or the like. In the present embodiment, the wireless communication unit of each body motion sensor 40 employs BTLE as a protocol for low power consumption communication, but can also employ, for example, ANT, ANT+, or the like. In addition, regular Bluetooth (registered trademark) can also be employed.

Note that, in the present embodiment, the system can be basically constructed within a range of near field communication between the information terminal device 100 and the body motion sensors 40, and the system can be operated as a so-called offline standalone system without being connected to a server or the like on a communication network during actual measurement.

(2) Information Terminal Device

FIGS. 4A and 4B illustrate an internal configuration of the information terminal device according to the present embodiment. The information terminal device 100 according to the present embodiment is, for example, a small terminal device such as a smartphone and may be a general rectangular terminal device, and can employ various types of terminal devices of a wearable terminal such as a wristwatch type, a stationary type, a mount type to be attached to the handlebars of a bicycle, and the like. Note that the information terminal device may be stored in a storage tool such as a bag when only recording body motion data during traveling.

Specifically, as illustrated in FIGS. 4A and 4B, the information terminal device 100 includes a wireless interface 113, a control unit 117, a memory 114, an output interface 111, and an input interface 112. More specifically, the information terminal device 100 according to the present embodiment has a function of collecting detection results detected by the body motion sensors 40, and can acquire the detection results by the body motion sensors 40 by the wireless interface 113 mutually communicating with the body motion sensors 40. The memory 114 of the information terminal device 100 functions as a body-motion recording unit that records the detection results by the body motion sensors 40 as body motion data. Here, the body motion data is raw data detected by various sensors, and data obtained by recording and analyzing the body motion data and extracting or correcting necessary information is body-motion reproduction data.

To the detection result transmitted from the each body motion sensor 40, sensor identification information for identifying each body motion sensor 40 is added, and the identification information is accumulated in the memory 114 of the information terminal device 100. Thus, when a detection result is acquired from the wireless interface 113, the control unit 117 can determine from which body motion sensor 40 the detection result is acquired. Note that the identification information includes attachment part information for identifying an attachment part of each sensor, and the body-motion reproduction data can be calculated based on the attachment part information. The body motion data further includes time information when the detection result is acquired from each body motion sensor 40.

The wireless interface 113 is a module that controls transmission and reception of various types of information via a communication network and near field communication such as WiFi and Bluetooth (registered trademark), communicates with each body motion sensor 40 using various protocols, and transmits and receives data to and from the server device or the like using 3G communication. The information terminal device 100 further includes an output interface 111 and an input interface 112. The input interface 112 is a device for inputting a user operation, such as a mouse, a keyboard, an operation button, or a touch panel. The output interface 111 includes a device that outputs video or audio, such as a display or a speaker. In particular, the output interface 111 includes a display unit such as a liquid crystal display, and the display unit is superimposed on a touch panel which is an input interface.

The display unit connected to the output interface 111 is an output device that displays or outputs an analysis result of the body-motion reproduction data, and displays display information generated by a display-information generation unit 117e through the output interface 111. The palm of a hand is displayed on a display built in the information terminal device 100 or an external display connected to the outside.

Meanwhile, the input interface 112 includes a moving-image acquisition unit 112a. The moving-image acquisition unit 112a is a module that acquires moving image data obtained by capturing and recording body motion of the wearer. The moving-image acquisition unit 112a is implemented by a general camera built in a smartphone or the like, and is used in order for the wearer to check a form by capturing an image of the wearer, and is also used to synchronize the body motion data acquired by a sensor as described later with a moving image captured by the camera. The moving image data acquired by the moving-image acquisition unit 112a includes video data in which a video is recorded, audio data recorded together with the video, and metadata such as time stamps of a capturing time, an end time, and time passage. The input interface 112 is connectable to a built-in camera 115 built in the information terminal device 100 and an external camera 20, and moving image data captured by these imaging means is acquired by the moving-image acquisition unit 112a, and accumulated in the memory 114 or used for processing in the control unit 117. Note that the moving image data acquired from the external camera 20 includes, in addition to streaming data sequentially acquired in real time at the time of capturing, moving image data in a file format captured and accumulated by the external camera 20 and downloaded and acquired after capturing.

In the present embodiment, the information terminal device 100 further has a function of analyzing the body motion of the wearer based on the body motion data acquired from each sensor and generating body-motion reproduction data. Specifically, as illustrated in FIGS. 4A and 4B, the information terminal device 100 includes the control unit 117, and the control unit 117 is an arithmetic processing device such as a CPU that performs various arithmetic operations necessary for controlling each unit. Note that each function of the information terminal device 100 is virtually constructed on the control unit 117 by the control unit 117 executing a stability evaluation program of the present invention. More specifically, the control unit 117 executes a stability evaluation application to virtually construct a body-motion-data acquisition unit 117a, a body-motion calculation unit 117b, an analysis unit 117d, and a display-information generation unit 117e.

The body-motion-data acquisition unit 117a is a module that acquires and records the body motion data from each body motion sensor 40 via the wireless interface 113. In the present embodiment, the body-motion-data acquisition unit 117a wirelessly communicates with each of the body motion sensors 40a to 40d to acquire the body motion data that is the detection results by them. The body-motion-data acquisition unit 117a functions as a body-motion-data recording unit, temporarily accumulates the body motion data in the memory 114, and transmits the detection result by each body motion sensor 40 to the body-motion calculation unit 117b.

The body-motion calculation unit 117b is a module that calculates the body motion of the wearer as the body-motion reproduction data based on the detection result by each of the body motion sensors 40*a* to 40*d* accumulated in the memory 114 that is the body-motion recording unit, such as the displacement and rotation of each of the body motion sensors 40*a* to 40*d*, and the acceleration thereof. Here, the detection result by each body motion sensor 40 is a value measured by a so-called 9-axis sensor and, in the present embodiment, is a direction and magnitude of acceleration (includes gravitational acceleration) acting on an object, an angular velocity (a magnitude, a direction, and a center position) of the object, and a magnitude and direction of a magnetic field.

Here, the calculated body motion includes, in the case of lifting weights in weight training, a movement or acceleration in the vertical direction, an angular velocity ω of relative rotation of the waist and the back, a temporal change in the angular velocity ω, and smoothness of the change. More specifically, in the present embodiment, the body motion sensors 40*a* and 40*b* are attached to the left and right thighs, and the body motion (single motion and repetitive motion) detected by the sensors is rotation and vertical motion of the thighs, the waist, and the back as illustrated in FIGS. 1A, 1B, 2A and 2B. The back moves up and down together with the waist and also performs rotational motion around the waist.

Furthermore, in the present embodiment, the body-motion calculation unit 117*b* includes a reference-value setting unit 118 that sets a stable reference value for evaluating the reproducibility of the body motion based on the body-motion reproduction data accumulated in the memory 114, and a reproducibility extraction unit 117*h* that calculates an amount of deviation from the reference-value setting unit 118 to analyze the reproducibility of the body motion.

The reference-value setting unit 118 sets, in an index calculation unit 117*g*, a value selected from an average value, a maximum value, a minimum value, or an arbitrary representative value within a predetermined period as a reference value based on the setting operation by the wearer 1. In the setting operation of the reference value, for example, by repeating the same motion several times at predetermined time intervals, and the average value, the minimum value, or the maximum value can be set, or the value at the time that the wearer 1 thinks the best can be set as an ideal value. In addition, any numerical value such as the ideal value of an advanced-level person or a professional can be input and set. In addition, in weight training or the like, for example, a value calculated based on body motion when the weight of the barbell is decreased or increased may be calculated and set based on body motion measured when the weight is increased or decreased.

To detailedly describe the function of setting the reference value by changing the load amount such as the weight, the reference-value setting unit 118 includes, regarding the function, a parameter presentation unit 118*a* and a load determination unit 118*b* in the present embodiment. The parameter presentation unit 118*a* is a module that assists the wearer 1 in setting the reference value and the threshold described above, and if a parameter is appropriately input when the reference value or the threshold for stability evaluation is set, the parameter presentation unit 118*a* acquires the parameter as a setting parameter, and guides an operator to appropriately input and set a setting parameter through a graphical user interface (GUI). For example, an instruction to change the weight of the barbell in weight training or the training load amount in a bicycle racing is presented to the wearer through the graphical user interface (GUI). When the load is properly applied according to the presentation, the parameter presentation unit 118*a* guides the wearer to set the parameter obtained from the load and the body motion of the wearer with respect to the load as the reference value or the threshold.

The load determination unit 118*b* is a module that monitors the setting parameter presented by the parameter presentation unit 118*a* during body motion detection to determine whether a certain load is applied. That is, the parameter presentation unit 118*a* described above specifies a parameter (change in the posture of the wearer, displacement/rotation of a predetermined body part, a weight of the barbell, vertical/horizontal displacement of the barbell, a speed, an acceleration, and the like) for applying a certain load to the wearer, and the load determination unit 118*b* monitors and determines whether the wearer is actually moving as specified.

Then, the reference-value setting unit 118 sets the reference value based on the body motion data related to the setting parameter in a state where the load determination unit 118*b* determines that the certain load is applied. For example, when the weight of the barbell is gradually increased by changing a parameter for applying the certain load, it is monitored whether the setting parameter such as the posture or the lifting pace of the wearer while the load is applied falls within a predetermined threshold, and the reference value for evaluating the stability is determined based on the body motion data when the threshold is exceeded. As a method of determining the reference value, there are various methods such as using a value when the parameter greatly changes as the maximum value (or minimum value) to set the value as the threshold of the upper limit (or lower limit), setting the median between the thresholds as the reference value, and setting a value at about 80% of the time when the parameter greatly changes as the reference value. The index calculation unit 117*g* refers to the index data based on the reference value or the threshold set in this manner to calculate the index for evaluating the stabilizing ability.

The parameter presentation unit 118*a* described above specifies a parameter (change in the posture of the wearer, displacement/rotation of a predetermined body part, an actual running speed of a bicycle, and the like) for applying the certain load to the wearer, and the load determination unit 118*b* monitors and determines whether the wearer is actually moving as specified.

Then, the reference-value setting unit 118 sets the reference value based on the body motion data related to the setting parameter in a state where the load determination unit 118*b* determines that the certain load is applied. For example, when the power to pedal the bicycle is gradually increased by changing the parameter for applying the certain load, it is monitored whether the setting parameter such as the posture or cadence of the wearer while the load is applied falls within a predetermined threshold, and the reference value for evaluating the stability is determined based on the body motion data when the threshold is exceeded. As a method of determining the reference value, there are various methods such as using a value immediately before the parameter exceeds the threshold as the reference value and setting a value at about 80% of the time when the parameter greatly changes. The index calculation unit 117*g* refers to the index data based on the reference value or the threshold set in this manner to calculate the index for evaluating the stabilizing ability.

In the present embodiment, the body-motion calculation unit 117*b* calculates the body motion of the wearer as the body-motion reproduction data based on the detection result by each body motion sensor 40 and the amount of deviation from the reference value of the body motion sensor 40. At this time, specifically, the body-motion calculation unit 117b calculates the relative displacement, speed, acceleration, and rotation (angular momentum) between the body motion sensors 40 based on the three-dimensional coordinates, speed, and acceleration of each body motion sensor 40. Then, based on the calculated relative displacement, speed, acceleration, and the like, the body-motion calculation unit 117b evaluates an instantaneous posture change in each of the left and right thighs of the wearer 1, relative displacement (distance or rotation) of the body parts, relative rotational motion of the back and the main parts, a timing of body motion, postural imbalance, and the like. Then, the body-motion reproduction data is calculated based on the trajectory of the displacement (body motion) of each body part calculated in this manner.

The analysis unit 117d is a module that analyzes each element of the body motion of the wearer 1 for each item based on the body-motion reproduction data. In the present embodiment, the analysis unit 117d functions as a characteristic analysis unit that analyzes characteristics of angular velocity change, amplitude of swing, and fluctuation of each body part extracted by the body-motion calculation unit 117b. The characteristics analyzed here are expressed as waveforms on a timeline defined by, for example, amplitude-time, and are synchronized with video data in which the wearer is recorded during exercising and then displayed or output by the output device via the display-information generation unit 117e.

Specifically, in the analysis by the analysis unit 117d in the present embodiment, the motion of lifting the barbell is analyzed. For example, in barbell squatting in which the wearer performs a bending and stretching motion in a posture of bearing the barbell as illustrated in FIGS. 1A, 1B, 2A and 2B, or in bench-press training in which the wearer lifts the barbell while lying on a training bench as illustrated in FIG. 3, the body-motion reproduction data is analyzed based on the relative displacement of the sensors, a change in angular velocity and angular acceleration, the weight of the barbell, the build of the wearer 1, and the like, and a temporal change in power, an interval, a break (non-motion time), a change in an upper body angle, a change in an angular range of a thigh, and the displacement of the lifted barbell in the X direction and the Y direction are estimated.

As another analysis method by the analysis unit 117d, three-dimensional data in which the wearer 1 is three-dimensionally displayed may be generated, or two-dimensional data projected on an XY plane may be generated. In addition, for example, body motion data serving as a model may be extracted from the memory 114 in which the body motion data serving as the model is accumulated, and compared with the body-motion reproduction data on the wearer to generate improvement data indicating a deviation from proper body motion or the like. Furthermore, by registering user information such as the gender, height, weight, and age in advance, analysis based on each user information may be performed. Then, the analysis unit 117d transmits an analysis result of the three-dimensional image data, the improvement data, and the like to the information terminal device 100.

Furthermore, in the present embodiment, the analysis unit 117d has a synchronous processing function, and the synchronous processing function performs calibration processing in order to perform synchronous processing for matching a time axis for displaying the body motion data with a time axis for displaying a video captured by the camera. Specifically, the synchronous processing function according to the present embodiment extracts a predetermined characteristic action (calibration action) by the wearer 1 who causes the body motion sensor 40 to react from the video or audio, extracts a characteristic reaction due to the characteristic action in the body motion data, and performs the synchronous processing by matching the timing of the extracted characteristic action with the timing of the characteristic reaction. The characteristic action includes, for example, an action of applying vibration a predetermined number of times to the body motion sensor 40 in a short time, such as vibration generated by the motion when placing a barbell 1a on a floor or a stand, tapping the bar of the barbell, or tapping or shaking the body motion sensor 40 itself a predetermined number of times.

As extraction processing of such a characteristic action, by, for example, detecting displacement of a predetermined shape or color with a constant amplitude or rhythm within a predetermined time length by image recognition processing and recognizing that the wearer 1 is performing an action of "placing the barbell" or "tapping the bar", the capturing time of a frame in the video having the maximum displacement during the time length is read, and the time information is detected as a calibration signal. In addition, when audio data is included in the moving image data, a sound of the wearer 1 tapping the bar may be extracted, and the extracted time information may be detected as the calibration signal.

Furthermore, when the recorded data has a size over a long period of time, an auxiliary user operation may be performed, and the characteristic action may be extracted by narrowing down to a time width designated by the user operation. In the meanwhile, the characteristic reaction of the body motion sensor 40 described above is detected by scanning detection values of various sensors provided in the body motion sensor 40, such as the acceleration sensor, and extracting a point where a reaction of a certain amplitude or more is repeated a predetermined number of times within a predetermined time width. Note that either the characteristic action or the characteristic reaction may be detected first, and the detection processing may be executed by narrowing the scanning range of the other with reference to the time stamp detected for the one.

Then, in order to match the timing of the extracted characteristic action with the timing of the characteristic reaction, the synchronization processing is performed by aligning the reproduction start times of both in such a manner that the time stamp (time information) at the time when the characteristic action described above has been performed and the time stamp at the time when the characteristic reaction has been detected are matched. At that time, if there is a difference in the intervals between repeatedly performed actions and reactions, the synchronization is performed by extending the reproduction time of the moving image or the length of the timeline of the body motion sensor and matching the reproduction start and end times of the moving image data and the body-motion reproduction data.

The display-information generation unit 117e is a module that generates display information to be displayed on the output interface 111, and generates display information for displaying or outputting the body-motion reproduction data analyzed by the analysis unit 117d corresponding to the moving image. In the present embodiment, the display information displays the moving image captured by the built-in camera 115 or the external camera 20 in a window W1, and displays the moving image in synchronization with the body-motion reproduction data analyzed by the analysis unit 117d and the timeline in a comparable manner. Note that the display information includes an audio signal and other output control signals together with the display data.

In addition, the display screen includes a graphical user interface (GUI) for a touch operation, and an operation on the touch panel on which the GUI is displayed is input to the input interface 112 to switch the display by the display-information generation unit 117e. For example, a moving image of the wearer 1 captured by the built-in camera 115 or the external camera 20 can be displayed on the screen, and each motion parameter included in the body-motion reproduction data can be individually displayed on the timeline. By switching the display mode, a moving image of the wearer 1 captured from the front by the built-in camera 115 of the information terminal device 100 can be displayed, and each motion parameter included in the body-motion reproduction data can be superimposed and displayed on the timeline. Note that, as other methods of switching the display mode, various methods such as superimposing a timeline on a moving image and displaying it on the full screen can be adopted.

The analysis unit 117d includes the index calculation unit 117g and a stability calculation unit 117f as modules related to stability evaluation processing. The stability calculation unit 117f is a module that calculates a stable reference value and evaluates the reproducibility of the body motion based on the amount of deviation from the stable reference value. The index calculation unit 117g is a module that refers to the index data based on the reference value or the threshold acquired from the recorded body motion data and calculates the index for evaluating the stabilizing ability. In the present embodiment, the index calculation unit 117g has a function of setting a value selected from an average value, a maximum value, a minimum value, or an arbitrary representative value within a predetermined period as the reference value based on a setting operation by the operator. At this time, the index data holds a correlation of the body motion of the wearer related to the bicycle movement during riding of a bicycle, the setting of the bicycle, the traveling speed or the traveling distance in bicycle racing, the input power transmitted to the wheels (or pedals), the cadence (rotation speed), and the like. Furthermore, the information held by the index data can include a correlation between the body motion of the wearer during competition (including all behaviors and actions involving body motion such as acting, playing, or training) and an incidence of injuries or failures during the competition.

The memory 114 is a storage device that records various types of data, and identification information for identifying each information terminal device 100, attachment part information on each body motion sensor 40, a relative positional relation of the body motion sensor 40 attached to each part, the user information described above, the body motion data serving as a model, and the like are accumulated therein. The memory 114 functions as a storage unit that stores the index data, and the index data is table data that holds a correlation between a stable period calculated by the stability calculation unit 117f, the amount of deviation after the stable period, and the index for evaluating the stabilizing ability.

(3) Regarding "parameter for applying a certain load"

Here, a "parameter for applying a certain load" is described.

(a) Weight Training

For example, the load in weight training directly includes the weight of a barbell itself, the number of times of lifting, and the like, and also includes parameters indirectly obtained by calculating or combining detection results of various sensors, such as the number of times of lifting per unit time, the required time per lifting, the vertical movement distance and speed, and horizontal displacement in the front-back or left-right direction due to vertical movement. The processing for presenting the setting parameter for "applying a certain load" includes, for example, specifying a gradual increase in barbell weight, specifying a sequential increase in the number of times of lifting per unit time, and regulating horizontal displacement during lifting.

Specifically, the parameter presentation unit 118a presents an instruction to change the weight of the barbell in weight training or the training load amount in bicycle racing to the wearer through a graphical user interface (GUI). When the load is properly applied according to the presentation, the parameter presentation unit 118a guides the wearer to set the parameter obtained from the load and the body motion of the wearer with respect to the load as the reference value or the threshold.

As the GUI of the parameter presentation unit 118a, in order to sequentially change the weight of the barbell from a light weight to a heavy weight in weight training, by presenting the weight of the barbell to be attached to the bar in numerals or the like, such as "Please change to 5 kg" or "Please change to 10 kg", the wearer is requested to confirm whether the change has been completed. Alternatively, the number of times of lifting the barbell, the required time (pace) for each squatting (vertical movement), and the like are also presented to the wearer through the graphical user interface (GUI) to guide the wearer to achieve an appropriate load by displaying or acoustically outputting the number of times of lifting and the pace of squatting counted by the sensor that detects vertical movement.

Then, the reference-value setting unit 118 sets the reference value based on the body motion data related to the setting parameter in a state where the load determination unit 118b determines that the certain load is applied. For example, when the weight of the barbell is gradually increased while the steady pace of squatting is maintained, it is monitored whether the posture or the squatting pace of the wearer while the load is applied falls within a predetermined threshold, and the reference value for evaluating the stability is determined based on the body motion data when the threshold is exceeded. As a method of determining the reference value, there are various methods such as using a value immediately before the parameter exceeds the threshold as the reference value and setting a value at about 80% of the time when the parameter greatly changes. The index calculation unit 117g refers to the index data based on the reference value or the threshold set in this manner to calculate the index for evaluating the stabilizing ability.

(b) Bicycle Racing

In bicycle racing, the direct load on the wearer is pedaling power (W), which is the propulsive force, and is calculated by torque x cadence (rotational speed). As a training method for improving this torque, there is slow frequency revolutions (SFR). SFR is generally a low-speed high-torque training program, in which a rider actually runs for a certain period of time under settings such as a cadence of 45 rpm at 115% of functional threshold power (FTP) that can be produced for one hour. Since such SFR is training with a high torque load, a rider tends to output the power by forcibly twisting the body or the like which is not done in low torque training, and the rider trains with a form different from that in normal running. Therefore, not only the target muscle strength is not developed due to the deviation from correct motion in low torque training, but also the risk of injuries increases.

For this reason, in the present embodiment, in training such as SFR, by measuring the motion of the waist at each torque while changing the torque load amount, the maximum torque that can be produced without changing the motion is defined as the upper limit of the optimal load, and this is used as the reference value to make the training more efficient and to reduce the risk of injury.

Therefore, the load in bicycle training such as the SFR is directly torque x cadence, but the indirect parameter can be indirectly obtained from static values, such as a tire circumferential length and a gear ratio, and dynamic values, such as an actual running speed of the bicycle. The processing for presenting the setting parameter for "applying a certain load" includes, for example, specifying a sequential increase or decrease in cadence, actual running speed, and input power by inputting the above static values such as a tire circumferential length and a gear ratio in advance, specifying a sequential increase or decrease in cadence per unit time, and changing the load according to the inclination by measuring the climbing inclination using an acceleration sensor or the like. In order to increase or decrease the cadence or the input power, it is preferable to specify that either is fixed, such as increasing the input power while the cadence is fixed or decreasing the cadence while the input power is fixed.

Specifically, in bicycle racing, as the GUI presented by the parameter presentation unit $118a$, the required time (pace) for one pedal revolution or the like is displayed or acoustically output through the graphical user interface (GUI) to increase cadence and to guide the wearer to achieve an appropriate load. Then, the reference-value setting unit $118$ sets the reference value or the threshold based on the body motion data related to the setting parameter in a state where the load determination unit $118b$ determines that the certain load is applied.

For example, when the power to pedal the bicycle is gradually increased, it is monitored whether the setting parameter, such as the posture or the cadence of the wearer, while the load is applied falls within a predetermined threshold, and the reference value for evaluating the stability is determined based on the body motion data when the threshold is exceeded. As a method of determining the reference value, there are various methods such as using a value immediately before the parameter exceeds the threshold as the reference value and setting a value at about 80% of the time when the parameter greatly changes. The index calculation unit $117g$ refers to the index data based on the reference value or the threshold set in this manner to calculate the index for evaluating the stabilizing ability.

(Stability Evaluation Method)

Figure 5:
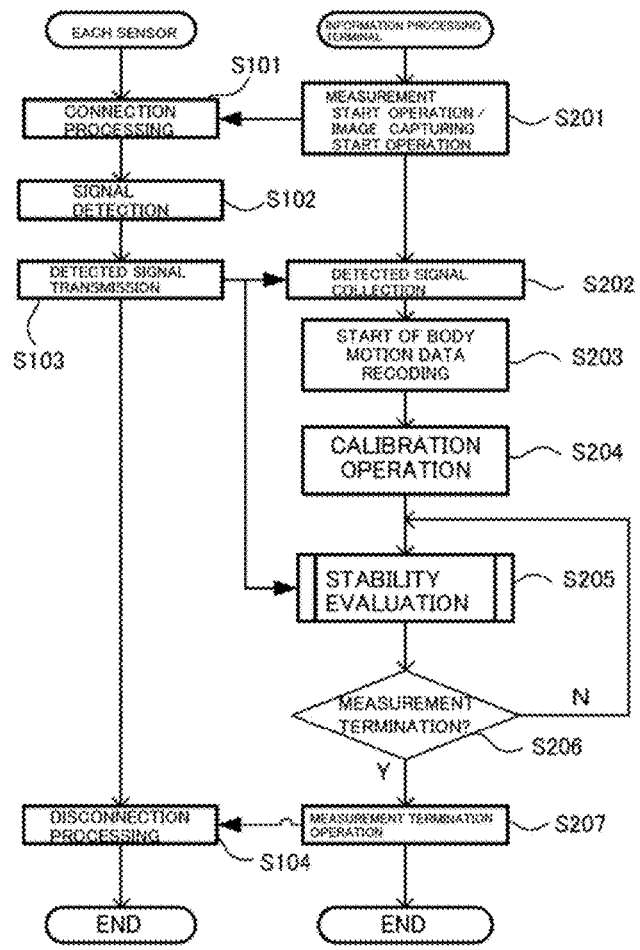
FIG. 5 is a sequence diagram illustrating a stability evaluation method according to an embodiment.
Figure 6:
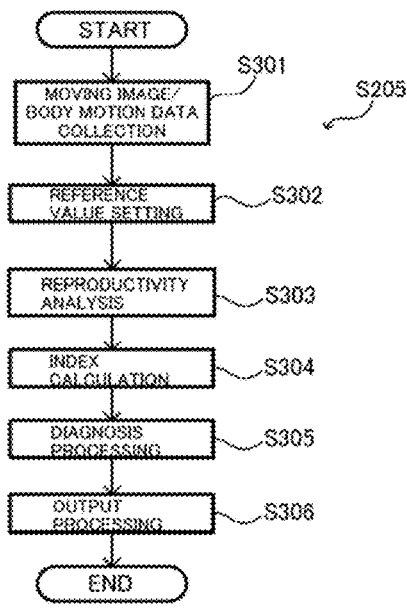
FIG. 6 is a flowchart illustrating stability evaluation processing according to an embodiment.

By operating the stability evaluation system having the above configuration, a stability evaluation method according to the present embodiment can be implemented. FIG. 5 illustrates a recording operation of the stability evaluation system, and FIG. 6 illustrates an operation at the time of data reproduction.

(1) Recording Operation

First, the wearer $1$ attaches the body motion sensors $40a$ to $40d$ (or $40e$ and $40f$) to arbitrary body parts such as the thighs, the waist, and the back, and equipment to be used such as the barbell $1a$. Note that, in the present embodiment, a camera built in an information terminal or an external camera is installed in such a manner as to capture an image of the wearer to capture the motion.

Then, an application which is a program of the present invention is started on the information terminal device $100$, a measurement start operation is input to the application to acquire a detection result from each body motion sensor $40$, and an image capturing start operation of the external camera $20$ is performed (S201). In response to the measurement start operation, the control unit $117$ of the information terminal device $100$ performs connection processing with each body motion sensor $40$ (S101). After the connection processing is performed, each body motion sensor $40$ starts detecting the motion of the wearer $1$ (S102). Specifically, the body motion sensor $40$ attached to each body part of the wearer detects three-dimensional displacement or acceleration of each part.

Next, each acquired detection result is transmitted to the wireless interface $113$ of the information terminal device $100$ by a weak radio wave via the wireless communication unit of each body motion sensor $40$ (S103). When the wireless interface $113$ of the information terminal device $100$ starts to acquire each detection result (S202), the memory $114$ which is the body-motion recording unit starts to record the detection results by the body motion sensors $40a$ to $40d$ as the body motion data, and sequentially records the detection signals continuously transmitted from each body motion sensor $40$ (S203).

At this time, the operator performs a calibration operation as necessary before competition such as bicycle riding is started (S204). Specifically, the operator performs an action of applying vibration a predetermined number of times to the body motion sensor $40$ in a short time, such as tapping the bar of the barbell $1a$ in front of the camera, or tapping or shaking the own body of the wearer $1$ or the body motion sensor $40$ itself a predetermined number of times.

Next, the competition is started, the detection values of the body motion sensors $40$ are continuously acquired during the competition to continuously perform the recording processing, and they are recorded as the body motion data in the memory $114$ or the like unless the measurement is terminated ("N" in S206).

The moving image data captured by the built-in camera $115$ built in the information terminal device $100$ or the external camera $20$ is acquired by the moving-image acquisition unit $112a$, and accumulated in the memory $114$ or used for processing in the control unit $117$. During this time, the detection data by the body motion sensors $40$ and the recorded video are analyzed in real time and displayed on the display unit of the information terminal device $100$. As one of the analyses, the stability evaluation is performed on the recorded body motion data (S205).

Then, the end of the competition is detected by, for example, detecting vibration generated by the motion such as placing the barbell $1a$ on the floor or a stand $1b$, the measurement is terminated ("Y" in S206), and the recording processing is stopped as necessary (S207). Then, the communication with each sensor is disconnected (S104).

(2) Stability Evaluation Processing

The stability evaluation in step S205 is described in detail. As illustrated in FIG. 6, the body motion data is collected by the body-motion-data acquisition unit $117a$, and the moving image data is collected by the moving-image acquisition unit $112a$ (S301). At this time, the reference value is set by the operation of the wearer $1$ (S302). Specifically, the reference-value setting unit $118$ sets, in response to the operation of the wearer $1$, the stable reference value for evaluating the reproducibility of the body motion based on the body-motion reproduction data accumulated in the memory $114$. Specifically, based on the setting operation by the wearer $1$, a value selected from an average value, a maximum value, a minimum value, or an arbitrary representative value within a predetermined period is set as the reference value. For example, in the setting operation of the reference value, for example, by repeating the same motion several times at predetermined time intervals, and the average value, the minimum value, or the maximum value can be set, or the value at the time that the wearer 1 thinks the best can be set as an ideal value. In addition, any numerical value such as the ideal value of an advanced-level person or a professional can be input and set.

In addition, in weight training or the like, for example, a value calculated based on body motion when the weight of the barbell is increased may be calculated and set based on body motion measured when the weight is decreased.

Then, the body-motion calculation unit 117b and the analysis unit 117d calculate and analyze the body motion of the wearer as the body-motion reproduction data based on the detection results by the body motion sensors 40 accumulated in the memory 114 and the relative positional relation between the body motion sensors 40. First, a reproducibility analyzing step is performed based on the body motion data recorded in the memory 114 (S303). At this time, for single motion, the reference value set by the operation by the user can be used as a stability reference value, and the reproducibility may be evaluated by comparing the amount of deviation from the stability reference value. For repetitive motion, an average value of the parameter related to the repetitive motion over a predetermined period (or a predetermined number of times) may be calculated as the stable reference value.

Then, an index calculation step, by the index calculation unit 117g, of referring to the index data according to the calculation result by the stability calculation unit 117f and calculating the index for evaluating the stabilizing ability is performed (S304). At this time, whether the amount of deviation from the stable reference value falls within a predetermined threshold may be monitored as needed, and a stable period during which the parameter of the body motion maintains the stable state may be calculated. For example, average values from the start of the competition are sequentially calculated, and the average value while the average values fall within a predetermined change amount is set as the stable reference value. The stable reference value is updated as needed, and an amount by which the current value deviates from the stable reference value is monitored as the amount of deviation as needed. Then, predetermined diagnosis processing is performed based on the calculated index, and a result of the diagnosis processing and the index are displayed or output together with the moving image and the body-motion reproduction data synchronized with them in a comparable manner by the display of the information terminal device 100 or the audio such as a speaker (S306).

(Stability Evaluation Program)

Note that the stability evaluation system and the stability evaluation method according to the present embodiment described above can be implemented by executing a stability evaluation program of the present invention described in a predetermined language on a computer as in the stability evaluation application described above. That is, by installing the program of the present invention in an IC chip or a memory device of a portable terminal device, a smartphone, a wearable terminal, a mobile PC, other information processing terminals, a general-purpose computer, such as a personal computer or a server computer, and executing the program by the CPU, a system having the above functions can be constructed, and the stability evaluation method can be performed.

(Operation and Effect)

According to the present embodiment, a stabilizing ability, so-called stability, according to a change in body motion of a wearer can be appropriately evaluated to achieve effective training, coaching, and fitting of athletic equipment. Specifically, conventionally, if the wearer is in an improper posture or motion that is likely to cause an injury or a failure in competition such as a barbell squat, it is possible to guide the wearer to have proper motion, a break, or the like or notify the wearer of an alert.

Note that the present invention is not limited to the above embodiment as it is, and the constituent elements can be modified and embodied without departing from the gist thereof in the implementation stage. In addition, various inventions can be formed by appropriately combining a plurality of constituent elements disclosed in the above embodiment. For example, some constituent elements may be deleted from all the constituent elements described in the embodiment.

Second Embodiment

Next, a second embodiment of the present invention will be described. In the present embodiment, the present invention using the information terminal device 100 described above is applied to bicycle racing to provide a system that enables body motion measurement and coaching in bicycle racing. More specifically, the gist of the present embodiment is, in addition to the configuration of the first embodiment described above, to extract a cyclical motion during body motion, set a reference value acquired within a predetermined period as a stable reference value based on a parameter related to the cyclical motion, and evaluate a stabilizing ability based on an amount of deviation from the stable reference value. In the present embodiment, the same constituent elements as those in the first embodiment described above are denoted by the same reference signs, the functions and the like thereof are the same unless otherwise specified, and the description thereof is omitted.

(Configuration of Stability Evaluation System)

Figure 7:
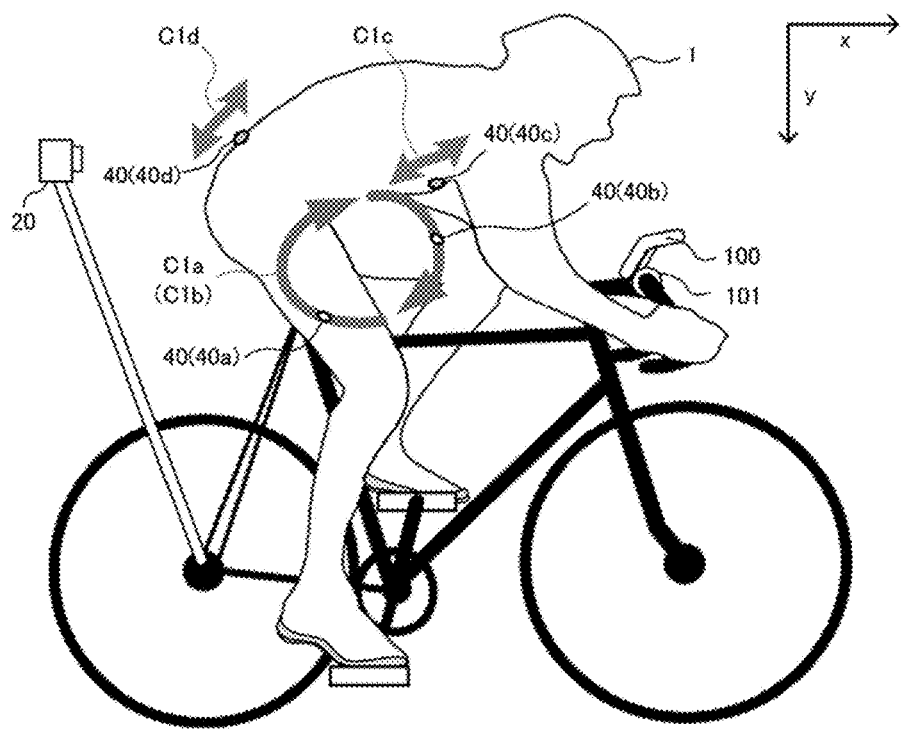
FIG. 7 is an explanatory diagram illustrating a usage mode of a stability evaluation system according to an embodiment.
Figure 8:
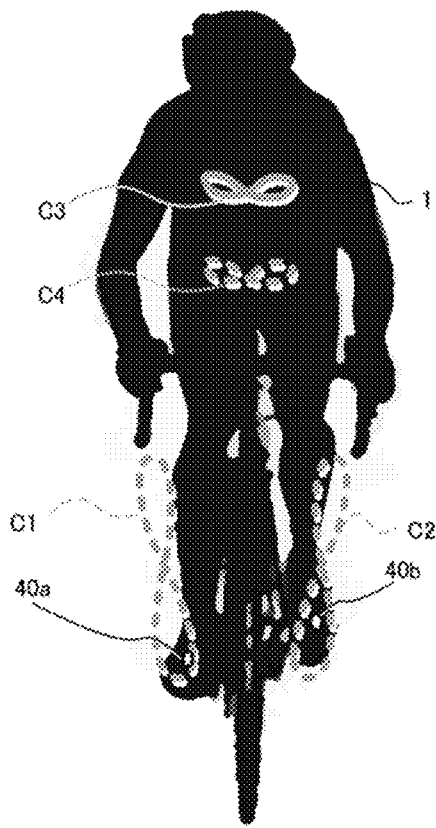
FIG. 8 is an example of body-motion reproduction data acquired in an embodiment.
Figure 9:
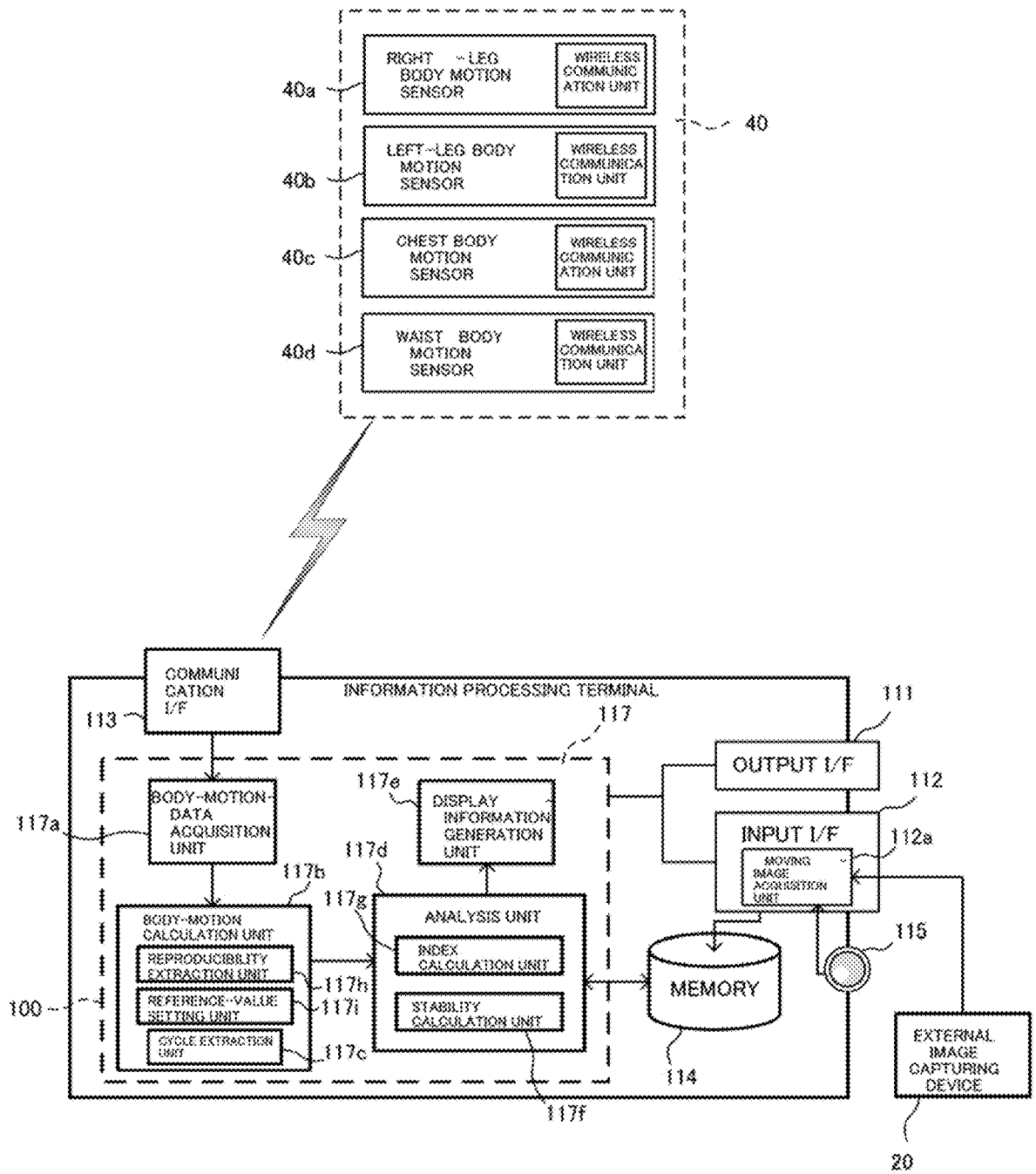
FIG. 9 is a block diagram illustrating an internal configuration of each device according to an embodiment.

FIG. 7 is an explanatory diagram illustrating a usage mode of a stability evaluation system using the information terminal device 100 according to the present embodiment. FIG. 8 is an example of body-motion reproduction data acquired by the stability evaluation system according to the present embodiment. FIG. 9 is a block diagram illustrating an internal configuration of each device.

As illustrated in FIGS. 7 to 9, the stability evaluation system according to the present embodiment includes the information terminal device 100 to be attached to a wearer 1, and body motion sensors 40 (40a to 40d) that are each attached to a body part of the wearer 1 and wirelessly connected to the information terminal device 100. Note that, in the present embodiment, the system can be basically constructed within a range of near field communication between the information terminal device 100 and the body motion sensors 40, and the system can be operated as a so-called offline standalone system without being connected to a server or the like on a communication network during actual measurement.

(Configuration of Each Device)

(1) Body Motion Sensor

The body motion sensors 40a to 40d are sensors that are attached to the body parts of the wearer 1 to exercise, and detect three-dimensional displacement or rotation of each part. In the present embodiment, the body motion sensors 40 include a right-leg body motion sensor 40a to be attached to the instep of the right foot of the wearer, a left-leg body motion sensor 40b to be attached to the instep of the left foot of the wearer, a chest body motion sensor 40c and a waist body motion sensor 40d to be attached to the chest and the waist of the wearer. These body motion sensors 40a to 40d are each equipped with a three-axis accelerometer that measures acceleration of an object, a three-axis gyroscope that detects angular velocity of the object, and a three-axis magnetic sensor that measures the magnitude and direction of a magnetic field, and can detect motion in nine axes. Note that each body motion sensor 40 can be attached to and detached from the shoes, belt, clothes of the wearer by a member such as a clip, and each sensor is easily attached to perform measurement, which makes continuous measurement easier without a burden on the wearer.

As illustrated in FIG. 9, each of the body motion sensors 40 (each of the body motion sensors 40a to 40d) includes a wireless communication unit. The wireless communication unit has an antenna inside, and can perform communication processing with the information terminal device 100 by a function of executing a data communication protocol for near field communication by Bluetooth (registered trademark) Low Energy (BTLE), Bluetooth (registered trademark) 4.0, or the like. In the present embodiment, the wireless communication unit of each body motion sensor 40 employs BTLE as a protocol for low power consumption communication, but can also employ, for example, ANT, ANT+, or the like. In addition, regular Bluetooth (registered trademark) can also be employed.

(2) Information Terminal Device

FIG. 9 illustrates an internal configuration of the information terminal device according to the present embodiment. The information terminal device 100 according to the present embodiment is basically the same as that described in the above embodiment. The information terminal device 100 according to the present embodiment also includes a control unit 117, and by executing a stability evaluation program according to the present invention, various functional modules are virtually constructed on the control unit 117. In the present embodiment, the control unit 117 executes a stability evaluation application to virtually construct a body-motion-data acquisition unit 117a, a body-motion calculation unit 117b, an analysis unit 117d, and a display-information generation unit 117e.

The body-motion-data acquisition unit 117a is a module that acquires and records the body motion data from each body motion sensor 40 via the wireless interface 113. In the present embodiment, the body-motion-data acquisition unit 117a wirelessly communicates with each of the body motion sensors 40a to 40d to acquire the body motion data that is the detection results by them. The body-motion-data acquisition unit 117a functions as a body-motion-data recording unit, temporarily accumulates the body motion data in the memory 114, and transmits the detection result by each body motion sensor 40 to the body-motion calculation unit 117b.

The body-motion calculation unit 117b is a module that calculates the body motion of the wearer as the body-motion reproduction data based on the detection result by each of the body motion sensors 40a to 40d accumulated in the memory 114 that is the body-motion recording unit, such as the displacement and rotation of each of the body motion sensors 40a to 40d, and the acceleration thereof. Here, the detection result by each body motion sensor 40 is a value measured by a so-called 9-axis sensor and, in the present embodiment, is a direction and magnitude of acceleration (includes gravitational acceleration) acting on an object, an angular velocity (a magnitude, a direction, and a center position) of the object, and a magnitude and direction of a magnetic field.

Here, the calculated body motion includes an index of smoothness of pedaling, an angular velocity ω of a pedal axis of a bicycle, a temporal change in the angular velocity ω, and smoothness of the change. In the present embodiment, the body motion sensors 40a and 40b are attached to the right and left shoes. As shown in FIG. 8, the rotational motion detected by the sensors is the rotation of the shoes, but the shoes rotate about the pedal axis in the case of pedaling a bicycle, and the angular velocity of the pedal axis is set to ω. In addition, the chest body motion sensor 40c and the waist body motion sensor 40d are attached to the chest and the waist of the wearer, and swing left and right (in the horizontal direction) in a plane orthogonal to the rotation plane of the pedal following the pedaling motion.

Furthermore, the body-motion calculation unit 117b in the present embodiment includes a cycle extraction unit 117c that extracts a cyclical change included in the body motion based on the body-motion reproduction data accumulated in the memory 114. The cyclical change includes not only a simple circular motion but also complicated free circular trajectories C1 to C4 that are three-dimensional and in which a figure-eight or wave-like motion is combined as illustrated in FIG. 8, and this circular trajectory is output as a waveform represented by amplitude and time. More specifically, in the present embodiment, the circular motion by the right-leg body motion sensor 40a attached to the instep of the right foot of the wearer 1 is extracted as C1, the circular motion by the left-leg body motion sensor 40b attached to the instep of the left foot of the wearer is extracted as C2, the swing of the chest of the wearer 1 is extracted as C3, and the swing of the waist is extracted as C4.

In the present embodiment, the body-motion calculation unit 117b calculates the body motion of the wearer as the body-motion reproduction data based on the detection result by each body motion sensor 40 and the change characteristic of the circular motion of each body motion sensor 40. At this time, for example, the body-motion calculation unit 117b calculates three-dimensional free circular trajectories C1 to C4 of the body motion sensors 40 as illustrated in FIG. 8. Then, the body-motion calculation unit 117b evaluates the circular motion of each of the left and right legs of the wearer and the amplitude, timing, imbalance, and the like of the swing of the main part based on the calculated characteristic changes in the free circular trajectories C1 to C4. Then, the body-motion reproduction data is calculated based on the free circular trajectories C1 to C4 calculated in this manner.

Figure 11A:
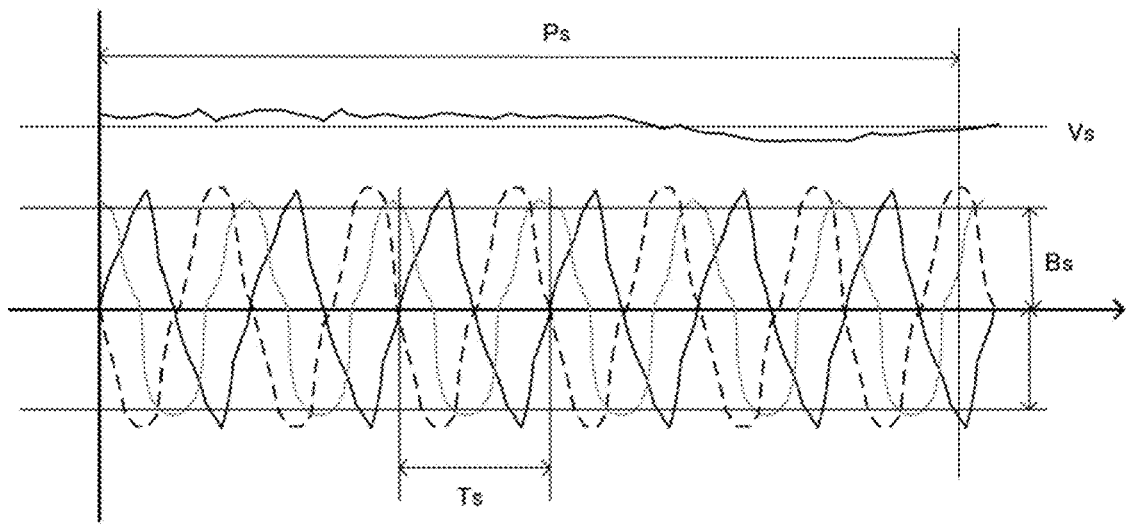
FIGS. 11A to 11C are explanatory diagrams illustrating stability evaluation processing according to an embodiment.
Figure 11B:
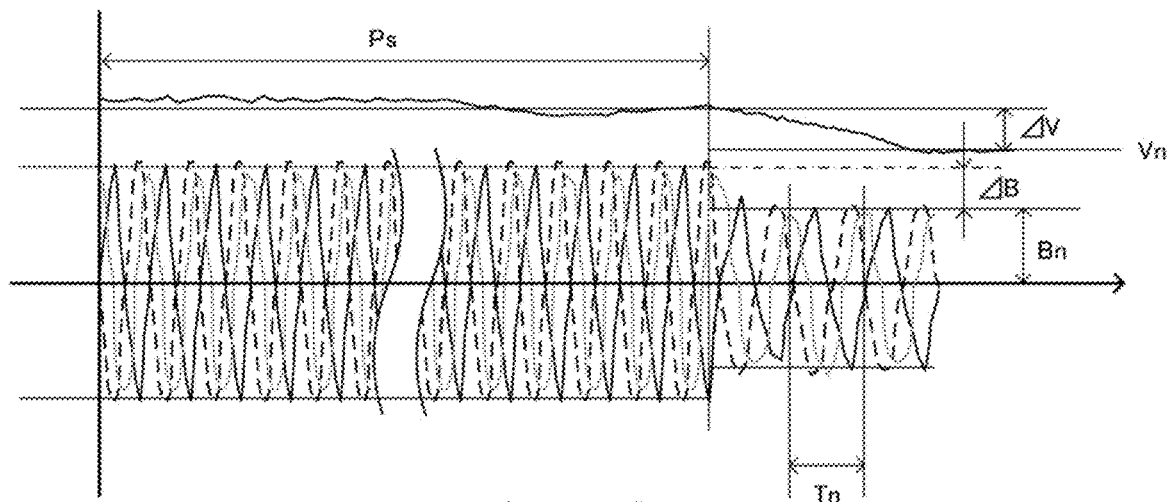
Figure 11C:
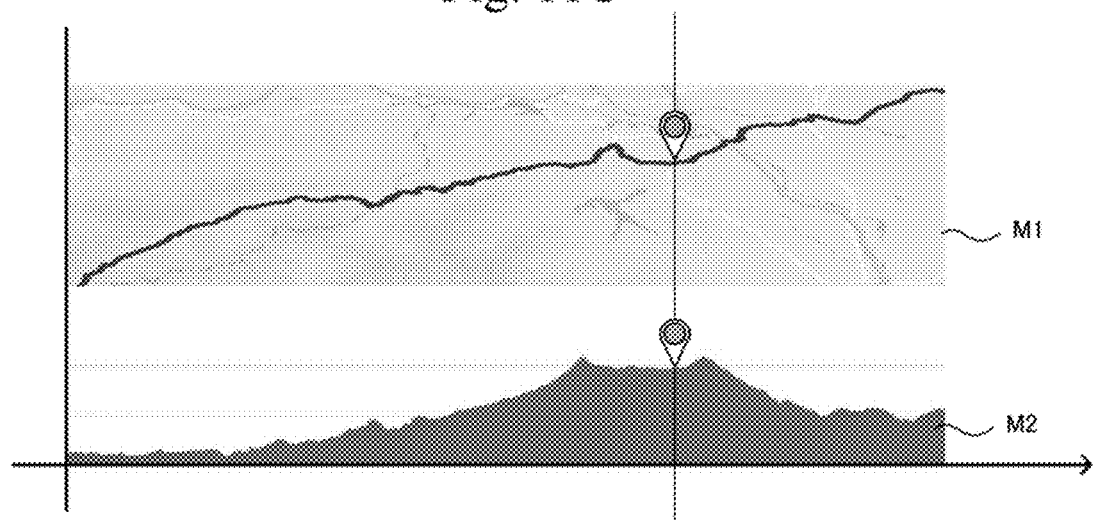

The analysis unit 117d is a module that analyzes each element of the body motion of the wearer 1 for each item based on the body-motion reproduction data. In the present embodiment, the analysis unit 117d functions as a characteristic analysis unit that analyzes characteristics of angular velocity change, amplitude of swing, and fluctuation in the cyclical motion extracted by the body-motion calculation unit 117b. The characteristics analyzed here are expressed as waveforms on a timeline defined by, for example, amplitude-time as illustrated in FIGS. 11A to 11C, and are synchronized with video data in which the wearer is recorded during riding or the like and position information on the map, and then displayed or output by the output device via the display-information generation unit 117e.

Specifically, in the analysis by the analysis unit 117d in the present embodiment, the motion of pedaling a bicycle, so-called pedaling, is analyzed. For example, the body-motion reproduction data is analyzed based on the relative displacement of the sensors, a change in angular velocity and angular acceleration, a pedal crank, the build of the wearer, and the like, and a temporal change in power, rhythm (cadence), a change in upper body angle (torso angle), a change in leg angular range (LAR) of a thigh, the displacement of right and left feet and knees in the X direction and the Y direction, and the displacement of the waist in the X direction and the Y direction are estimated.

As another analysis method by the analysis unit 117d, three-dimensional data in which the wearer 1 is three-dimensionally displayed may be generated, or two-dimensional data projected on an XY plane may be generated. In addition, for example, body motion data serving as a model may be extracted from the memory 114 in which the body motion data serving as the model is accumulated, and compared with the body-motion reproduction data on the wearer to generate improvement data indicating a deviation from proper body motion or the like. Furthermore, by registering user information such as the gender, height, weight, and age in advance, analysis based on each user information may be performed. Then, the analysis unit 117d transmits an analysis result of the three-dimensional image data, the improvement data, and the like to the information terminal device 100.

Furthermore, in the present embodiment, the analysis unit 117d has a synchronous processing function, and the synchronous processing function performs calibration processing in order to perform synchronous processing for matching a time axis for displaying the body motion data with a time axis for displaying a video captured by the camera. Specifically, the synchronous processing function according to the present embodiment extracts a predetermined characteristic action (calibration action) by the wearer 1 who causes the body motion sensor 40 to react from the video or audio, extracts a characteristic reaction due to the characteristic action in the body motion data, and performs the synchronous processing by matching the timing of the extracted characteristic action with the timing of the characteristic reaction. The characteristic action includes, for example, an action of applying vibration a predetermined number of times to the body motion sensor 40 in a short time, such as tapping or shaking the own body of the wearer 1 or the body motion sensor 40 itself a predetermined number of times in front of the camera.

As extraction processing of such a characteristic action, by, for example, detecting displacement of a predetermined shape or color with a constant amplitude or rhythm within a predetermined time length by image recognition processing and recognizing that the wearer 1 is performing an action of "tapping with a hand", the capturing time of a frame in the video having the maximum displacement during the time length is read, and the time information is detected as a calibration signal. In addition, when audio data is included in the moving image data, a sound of the wearer 1 tapping the bar may be extracted, and the extracted time information may be detected as the calibration signal.

Furthermore, when the recorded data has a size over a long period of time, an auxiliary user operation may be performed, and the characteristic action may be extracted by narrowing down to a time width designated by the user operation. In the meanwhile, the characteristic reaction of the body motion sensor 40 described above is detected by scanning detection values of various sensors provided in the body motion sensor 40, such as the acceleration sensor, and extracting a point where a reaction of a certain amplitude or more is repeated a predetermined number of times within a predetermined time width. Note that either the characteristic action or the characteristic reaction may be detected first, and the detection processing may be executed by narrowing the scanning range of the other with reference to the time stamp detected for the one.

Then, in order to match the timing of the extracted characteristic action with the timing of the characteristic reaction, the synchronization processing is performed by aligning the reproduction start times of both in such a manner that the time stamp (time information) at the time when the characteristic action described above has been performed and the time stamp at the time when the characteristic reaction has been detected are matched. At that time, if there is a difference in the intervals between repeatedly performed actions and reactions, the synchronization is performed by extending the reproduction time of the moving image or the length of the timeline of the body motion sensor and matching the reproduction start and end times of the moving image data and the body-motion reproduction data.

The display-information generation unit 117e is a module that generates display information to be displayed on the output interface 111, and generates display information for displaying or outputting the body-motion reproduction data analyzed by the analysis unit 117d corresponding to the moving image. In the present embodiment, the display information displays the moving image captured by the built-in camera 115 or the external camera 20 in a window on the display, expresses the body-motion reproduction data analyzed by the analysis unit 117d in a planar circle, and displays the moving image in synchronization with the body-motion reproduction data analyzed by the analysis unit 117d and the timeline to be displayed in a comparable manner. Note that the display information includes an audio signal and other output control signals together with the display data.

In addition, the display screen includes a graphical user interface (GUI) for a touch operation, and an operation on the touch panel on which the GUI is displayed is input to the input interface 112 to switch the display by the display-information generation unit 117e. For example, a moving image of the wearer 1 captured by the built-in camera 115 or the external camera 20 can be displayed on the screen, and each motion parameter included in the body-motion reproduction data can be individually displayed on the timeline. By switching the display mode, a moving image of the wearer 1 captured from the front by the built-in camera 115 of the information terminal device 100 can be displayed, and each motion parameter included in the body-motion reproduction data can be superimposed and displayed on the timeline. Note that, as other methods of switching the display mode, various methods such as superimposing a timeline on a moving image and displaying it on the full screen can be adopted.

The analysis unit 117d includes the index calculation unit 117g and a stability calculation unit 117f as modules related to stability evaluation processing. The stability calculation unit 117f is a module that calculates an average value of the parameter related to the cyclical motion extracted by the cycle extraction unit 117c over a predetermined period as a stable reference value, and calculates a stable period during which the stable state of the cyclical motion is continued based on the amount of deviation from the stable reference value. The index calculation unit 117g is a module that refers to the index data according to the calculation result by the stability calculation unit 117f and calculates the index for evaluating the stabilization ability.

Note that, when the synchronized moving image and the body-motion reproduction data are synchronized and output in a comparable manner, by sliding a reproduction point cursor on the timeline to the left and right to designate a reproduction time, the frame in the moving image at the time indicated by the timeline may be displayed. The reproduction point cursor can move on the timeline in synchronization with the reproduction of the moving image to display the time progression, and can designate the reproduction start point to start the reproduction of the moving image from that point, or can set a predetermined time width to repeatedly reproduce the moving image during that time.

The memory 114 is a storage device that records various types of data, and identification information for identifying each information terminal device 100, attachment part information on each body motion sensor 40, a relative positional relation of the body motion sensor 40 attached to each part, the user information described above, the body motion data serving as a model, and the like are accumulated therein. The memory 114 functions as a storage unit that stores the index data, and the index data is table data that holds a correlation between a stable period calculated by the stability calculation unit 117f, the amount of deviation after the stable period, and the index for evaluating the stabilizing ability.

(Stability Evaluation Method)

Figure 10:
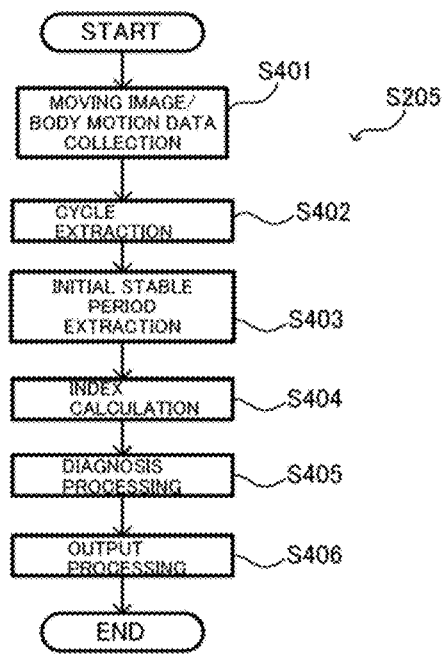
FIG. 10 is a flowchart illustrating stability evaluation processing according to an embodiment.

By operating the stability evaluation system having the above configuration, a stability evaluation method according to the present embodiment can be implemented. FIG. 10 illustrates an operation at the time of data reproduction. Note that, in the present embodiment, the recording operation is similar to that in the first embodiment described above, as illustrated in FIG. 10.

In the stability evaluation processing in the present embodiment, as illustrated in FIG. 10, the body motion data is collected by the body-motion-data acquisition unit 117a, and the moving image data is collected by the moving-image acquisition unit 112a (S401). Then, the body-motion calculation unit 117b and the analysis unit 117d calculate and analyze the body motion of the wearer as the body-motion reproduction data based on the detection results by the body motion sensors 40 accumulated in the memory 114 and the relative positional relation between the body motion sensors 40.

First, a cycle extraction step of extracting a cyclical motion of each body motion sensor 40 is performed based on the body motion data recorded in the memory 114 (S402). Next, an average value of the parameter related to the cyclical motion extracted by the cycle extraction unit 117c over a predetermined period is calculated as the stable reference value. For example, as illustrated in FIG. 11A, an average of the cycles while a stable cycle is maintained is calculated as a stable cycle Ts, an average of the amplitudes is calculated as a stable amplitude Bs, and a period (time length) during which stability is maintained is calculated as Ps. In the present embodiment, the moving speed of the wearer is also measured, and the speed is also measured as a stable speed Vs.

Next, a stability calculation step of monitoring as needed whether the amount of deviation (ΔT, ΔB, and ΔV in the drawing) from the stable reference value (Ts, Bs, Vs, and the like) falls within a predetermined threshold and calculating the stable period Ps during which the parameter of the cyclical motion maintains the stable state is performed (S403). Here, average values from the start of the competition are sequentially calculated, and the average value while the average values fall within a predetermined change amount is set as the stable reference value. The stable reference value is updated as needed, and an amount by which the current value deviates from the stable reference value is monitored as the amount of deviation as needed.

Then, an index calculation step, by the index calculation unit 117g, of referring to the index data according to the calculation result by the stability calculation unit 117f and calculating the index for evaluating the stabilizing ability is performed (S404). This index data holds a correlation between the initial stable period Ps calculated by the stability calculation unit 117f, the amount of deviation after the stable period Ps, and the index for evaluating the stabilizing ability. Then, predetermined diagnosis processing is performed based on the calculated index (S405), and a result of the diagnosis processing and the index are displayed or output together with the moving image and the body-motion reproduction data synchronized with them in a comparable manner by the display of the information terminal device 100 or the audio such as a speaker (S406). At this time, for example, the duration of the stable period and the transition of the amount of deviation may be displayed on maps M1 and M2 based on the diagnosis result and the speed every moment, as illustrated in FIG. 11C.

(Index Data)

Examples of the above index data include the following.

(1) Bicycle Fitting

For example, the index data can be a correlation between body motion of the wearer during bicycle riding and fitting that is setting of the bicycle. More specifically, the fitting such as the height of the saddle of the bicycle, the position of the pedals, the height and angle of the handlebars, and the like is set while checking whether the form and the speed at the time of riding can be stably maintained for a certain period of time or more by referring to the time length in which the stable period Ps is continued. Specifically, the body motion data is recorded while the wearer with the body motion sensor 40 is actually riding the bicycle, displacement in the chest and waist, an angle change, an angular velocity, an angular acceleration, and the like are monitored as parameters of the cyclical motion, and a change in a right-left difference in the angular ranges of the thighs (comparison of the sensor values) is monitored.

At this time, the angle difference between the waist and the chest is continuously measured (environmental dependency is eliminated by taking the angle difference of the points) to check how much the initial value set in the bike fitting can be maintained. The stable period Ps during which the initial value can be continuously maintained, that is, the stable period Ps during which the initial value falls within the upper and lower thresholds (±%) is inspected, and the amount of deviation is measured. Then, by referring to the index data based on these, the wearer is urged to review the result of the original bike fitting when the initial value cannot be maintained.

(2) Bicycle Racing

As an example of other index data, a difference between the angle of the head and the angle of the chest of the wearing vehicle may be monitored in order to maintain constant motion during bicycle racing. Specifically, the body motion sensors 40 are attached to the waist, chest, and both thighs of the wearer, and the body motion is detected from the start of the bicycle riding. In this case, the wearer rides the bicycle in units of seconds at a stable location, and the initial stable period is repeatedly measured to set a more-stable initial stable reference value in units of seconds.

Then, the wearer starts long-distance actual riding, and the body motion data is monitored in real time. Then, when the amount of deviation from the stable reference value exceeds a predetermined threshold, an alert is output as abnormality detection. In the determination of the abnormality detection, the amount of deviation (±%) of the single sensor data from the initial value or the calculated value (MPI), the amount of deviation (±%) from the initial value related to the mutual relation of the parameters from the sensors, and the like may be set by operation of the user without a cent. In addition, for the body motion data recorded in this manner, the best score of the athlete may be defined from the past data.

This guides the athlete to maintain the form and concentrate on riding until the end of the race when the athlete is conventionally tired after the start of the race and is in an imbalanced form, such as riding in a form that is aerodynamically disadvantageous, in the latter half of the race. Here, since the initial stable period is set based on riding in seconds, it is possible to perform measurement regardless of geographical features.

(3) Running

In addition to bicycle racing, it is possible to similarly evaluate the stability of the form in competition such as running. For example, the index data may hold a correlation between the body motion of the wearer during running and the stability of the form during running or an incidence of injuries or failures. In running, the stable reference value for repetitive motion is calculated, and the index data is referred to by monitoring deviation from the stable reference value. Then, an incidence of injuries or failures according to the amount of deviation is calculated, and when the possibility of occurrence of injuries or the like increases, an abnormal value is notified to the wearer. At this time, an abnormal value may be eliminated through operation determination processing.

Specifically, the body motion sensors 40 are attached to the back, the waist, the chest, and the thighs, and the angle of the knee adduction at the time of landing, the angle difference between the waist and the chest, the swing back angle of the legs, the manner of landing, and the like are monitored. Accordingly, by detecting an imbalanced form, such as lifting the chin, during running and notifying the wearer of an alert to coach the wearer to slow down and maintain the form. The correlation of the stable period, the reference value, the amount of deviation, the excessive pace that is likely to lead to an injury, and the consumption of stamina is held in the index data, and the significant changes in the parameter values due to the imbalanced form when the wearer tries to increase the running speed beyond the capacity is detected to coach the wearer to stop trying to an unreasonable speed that cannot be maintained.

Here, a method of monitoring the "manner of landing" in running includes, for example, a method in which the body motion sensors are attached to the insteps of the left and right feet, and acceleration, angular velocity, and the like applied to each leg are detected to recognize the landing impact during running and the motion immediately after landing from the subsequent rotation of the body motion sensors. Accordingly, it is possible to detect a change in the form of the wearer due to fatigue or the like and a change in the manner of landing of the leg itself can also be detected. Specifically, in the monitoring of the running form, the area below the ankle that lands first is focused on.

This manner of landing is classified into three types of toe landing (forefoot strike), flat landing (midfoot strike), and heel landing (rearfoot strike). In these manners of landing, vibration due to a landing impact, angular velocity at and after the landing, and rotational acceleration (gyro data) immediately after the landing are used to measure a change in running form, including landing, by comparing the amount of deviation of these parameters from the reference values and the threshold. Then, the degree of fatigue, an incidence of injuries, and the like are obtained by referring to the index data based on the comparison result of the amount of deviation and the threshold, and it is possible to properly coach the wearer and to notify the wearer of an alert. Also in this case, as the setting of the reference value and the threshold for the manner of landing, a value at the start of running, or an average value for a certain period of stable time, a maximum value, or a minimum value may be used. Furthermore, the load may be varied by changing the climbing gradient or the running pace (speed), and each parameter at the time when the form is imbalanced may be set as the maximum or minimum threshold, or the average value of the period until that point may be set as the reference value.

(Stability Evaluation Program)

Note that the stability evaluation system and the stability evaluation method according to the present embodiment described above can be implemented by executing a stability evaluation program of the present invention described in a predetermined language on a computer as in the stability evaluation application described above. That is, by installing the program of the present invention in an IC chip or a memory device of a portable terminal device, a smartphone, a wearable terminal, a mobile PC, other information processing terminals, a general-purpose computer, such as a personal computer or a server computer, and executing the program by the CPU, a system having the above functions can be constructed, and the stability evaluation method can be performed.

(Operation and Effect)

According to the present embodiment, a stabilizing ability, so-called stability, according to a change in body motion of a wearer can be appropriately evaluated to achieve effective training, coaching, and fitting of athletic equipment. Specifically, during bicycle racing or fitting, it is possible to guide the athlete to maintain the form and concentrate on running until the end of the competition when the athlete is conventionally tired after the start of running and is in an imbalanced form, such as running in a form that is aerodynamically disadvantageous, in the latter half of the competition, and to notify the athlete of an alert when an injury or failure is likely to occur.

In the present embodiment, the length of the stable period during which the reference value, the threshold, and the stable reference value are maintained is detected to evaluate whether the stability of the body motion is secured or the body motion is correctly reproduced. Therefore, by appropriately setting the reference value, the width of the threshold, or the like, it is possible to detect a small change before the form is visibly imbalanced and coach the wearer to make small correction to maintain the stability.

In addition, the stability evaluation program according to the present embodiment can be distributed via, for example, a communication line, and can be transferred as a packaged application that operates on a standalone computer by being recorded on a computer-readable recording medium. Specifically, as the recording medium, a magnetic recording medium such as a flexible disk or a cassette tape, an optical disk such as a CD-ROM or a DVD-ROM, or various recording media such as a RANI card can be used to record the program. Then, according to a computer-readable recording medium recording the program, the above system and method can be easily implemented using a general-purpose computer or a dedicated computer, and the program can be easily stored, transported, and installed.

Note that the present invention is not limited to the above embodiment as it is, and the constituent elements can be modified and embodied without departing from the gist thereof in the implementation stage. In addition, various inventions can be formed by appropriately combining a plurality of constituent elements disclosed in the above embodiment. For example, some constituent elements may be deleted from all the constituent elements described in the embodiment.

EXPLANATION OF SYMBOLS

C1 to C4 Free rotation/swing trajectory
PP Reproduction point cursor
W1 Window
W2 Timeline
W3 GUI
X Traveling direction
Y Vertical direction
1 Wearer
20 External camera
40 Body motion sensor
40a Right-leg body motion sensor
40b Left-leg body motion sensor
40c Chest body motion sensor
40d Waist body motion sensor
40e, 40f Barbell body motion sensor
100 Information terminal device
111 Output interface
112 Input interface
112a Moving image acquisition unit
113 Wireless interface
114 Memory
115 Built-in camera
117 Control unit
117a Body-motion-data acquisition unit
117b Body-motion calculation unit
117c Cycle extraction unit
117d Analysis unit
117e Display-information generation unit
117f Stability calculation unit
117g Index calculation unit
117h Reproducibility extraction unit
118 Reference-value setting unit
118a Parameter presentation unit
118b Load determination unit

What is claimed is:

1. A stability evaluation system configured to detect body motion of a wearer and evaluate a stabilizing ability according to a change in the body motion, the system comprising:
a plurality of body motion sensors that is attached to the wearer or an arbitrary part of equipment to be used by the wearer and is capable of detecting three-dimensional displacement or rotation of each part;
a body-motion recording unit configured to record a detection result by the plurality of body motion sensors as body motion data;
a storage unit configured to store index data holding a correlation between an amount of deviation from a reference value for evaluating reproducibility of the body motion and an index for evaluating the stabilizing ability;
an index calculation unit configured to refer to the index data based on a reference value or a threshold acquired from the body motion data recorded in the body-motion recording unit and calculate the index for evaluating the stabilizing ability; and
an output device configured to display or output the index calculated by the index calculation unit.

2. The stability evaluation system according to claim 1, further comprising:
a parameter presentation unit configured to acquire a parameter for applying a certain load to the wearer or the arbitrary part of the equipment to be used by the wearer as a setting parameter and present the acquired setting parameter to the wearer;
a load determination unit configured to monitor the setting parameter presented by the parameter presentation unit and determine whether the certain load is applied; and
a reference-value setting unit configured to set a reference value or a threshold based on body motion data related to the setting parameter in a state where the load determination unit determines that the certain load is applied, wherein
the index calculation unit refers to the index data based on the reference value or the threshold set by the reference-value setting unit and calculates the index for evaluating the stabilizing ability.

3. The stability evaluation system according to claim 1 or 2, further comprising a stability calculation unit configured to calculate, based on an amount of deviation from the acquired reference value, a stable period during which a stable state of the body motion is continued, wherein
the storage unit stores, as the index data, a correlation between the stable period calculated by the stability calculation unit, the amount of deviation after the stable period, and the index for evaluating the stabilizing ability, and
the index calculation unit refers to the index data according to a calculation result by the stability calculation unit and calculates the index for evaluating the stabilizing ability.

4. The stability evaluation system according to claim 1, wherein the index calculation unit sets, as the reference value, a value selected from an average value, a maximum value, a minimum value, or an arbitrary representative value within the predetermined period based on a setting operation by an operator.

5. The stability evaluation system according to claim 1, further comprising:
a cycle extraction unit configured to extract cyclical motion of each of the plurality of body motion sensors based on the body motion data recorded in the body-motion recording unit; and
a stability calculation unit configured to set, as a stable reference value, a reference value acquired within a predetermined period based on a parameter related to the cyclical motion extracted by the cycle extraction unit and calculate, based on an amount of deviation from the stable reference value, a stable period during which a stable state of the cyclical motion is continued, wherein
the storage unit stores, as the index data, a correlation between the stable period calculated by the stability calculation unit, the amount of deviation after the stable period, and the index for evaluating the stabilizing ability, and
the index calculation unit refers to the index data according to a calculation result by the stability calculation unit and calculates the index for evaluating the stabilizing ability.

6. The stability evaluation system according to claim 1, wherein the index data holds a correlation between body motion of the wearer during competition and an incidence of injuries or failures during the competition.

7. A stability evaluation program to detect body motion of a wearer and evaluate a stabilizing ability according to a change in the body motion using a plurality of body motion sensors that is attached to the wearer or an arbitrary part of equipment to be used by the wearer and is capable of detecting three-dimensional displacement or rotation of each part, the stability evaluation program causing an information processing terminal to function as:
- a body-motion recording unit configured to record a detection result by the plurality of body motion sensors as body motion data;
- a storage unit configured to store index data holding a correlation between an amount of deviation from a reference value for evaluating reproducibility of the body motion and an index for evaluating the stabilizing ability;
- an index calculation unit configured to refer to the index data based on a reference value or a threshold acquired from the body motion data recorded in the body-motion recording unit and calculate the index for evaluating the stabilizing ability; and
- an output device configured to display or output the index calculated by the index calculation unit.

8. The stability evaluation program according to claim 7, causing the information processing terminal to further function as:
- a parameter presentation unit configured to acquire a parameter for applying a certain load to the wearer or the arbitrary part of the equipment to be used by the wearer as a setting parameter and present the acquired setting parameter to the wearer;
- a load determination unit configured to monitor the setting parameter presented by the parameter presentation unit and determine whether the certain load is applied; and
- a reference-value setting unit configured to set the reference value based on body motion data related to the setting parameter in a state where the load determination unit determines that the certain load is applied, wherein
- the index calculation unit refers to the index data based on the reference value or the threshold set by the reference-value setting unit and calculates the index for evaluating the stabilizing ability.

9. The stability evaluation program according to claim 7, causing the information processing terminal to further function as a stability calculation unit configured to calculate, based on an amount of deviation from the acquired reference value, a stable period during which a stable state of the body motion is continued, wherein
- the storage unit stores, as the index data, a correlation between the stable period calculated by the stability calculation unit, the amount of deviation after the stable period, and the index for evaluating the stabilizing ability, and
- the index calculation unit refers to the index data according to a calculation result by the stability calculation unit and calculates the index for evaluating the stabilizing ability.

10. The stability evaluation program according to claim 7, wherein the index calculation unit sets, as the reference value, a value selected from an average value, a maximum value, a minimum value, or an arbitrary representative value within the predetermined period based on a setting operation by an operator.

11. The stability evaluation program according to claim 7, causing the information processing terminal to further function as:
- a cycle extraction unit configured to extract cyclical motion of each of the plurality of body motion sensors based on the body motion data recorded in the body-motion recording unit; and
- a stability calculation unit configured to set, as a stable reference value, a reference value acquired within a predetermined period based on a parameter related to the cyclical motion extracted by the cycle extraction unit and calculate, based on an amount of deviation from the stable reference value, a stable period during which a stable state of the cyclical motion is continued, wherein
- the storage unit stores, as the index data, a correlation between the stable period calculated by the stability calculation unit, the amount of deviation after the stable period, and the index for evaluating the stabilizing ability, and
- the index calculation unit refers to the index data according to a calculation result by the stability calculation unit and calculates the index for evaluating the stabilizing ability.

12. The stability evaluation program according to claim 7, wherein the index data holds a correlation between body motion of the wearer during competition and an incidence of injuries or failures during the competition.

13. A stability evaluation method to detect body motion of a wearer and evaluate a stabilizing ability according to a change in the body motion, the method comprising:
- a body-motion recording step of measuring, by a plurality of body motion sensors attached to the wearer or an arbitrary part of equipment to be used by the wearer, three-dimensional displacement or rotation of each part and recording a detection result by the plurality of body motion sensors as body motion data in a body-motion recording unit;
- an index calculation step, by an index calculation unit, of referring to index data holding a correlation between an amount of deviation from a stable reference value for evaluating reproducibility of the body motion and an index for evaluating the stabilizing ability and calculating the index for evaluating the stabilizing ability based on a reference value or a threshold acquired from the body motion data recorded in the body-motion recording unit; and
- an output step, by an output device, of displaying or outputting the index calculated in the index calculation step.

14. The stability evaluation method according to claim 13, further comprising:
- a parameter presentation step, by a parameter presentation unit, of acquiring a parameter for applying a certain load to the wearer or the arbitrary part of the equipment to be used by the wearer as a setting parameter and presenting the acquired setting parameter to the wearer;
- a load determination step, by a load determination unit, of monitoring the setting parameter presented by the parameter presentation unit and determining whether the certain load is applied; and
- a reference-value setting step, by a reference-value setting unit, of setting the reference value based on body motion data related to the setting parameter in a state where the load determination unit determines that the certain load is applied, wherein the index calculation unit refers to the index data based on the reference value or the threshold set by the reference-value setting unit and calculates the index for evaluating the stabilizing ability in the index calculation step.

15. The stability evaluation method according to claim 13, further comprising a stability calculation step, by a stability calculation unit, of calculating, based on an amount of deviation from the acquired reference value, a stable period during which a stable state of the body motion is continued, wherein the storage unit stores, as the index data, a correlation between the stable period calculated by the stability calculation unit, the amount of deviation after the stable period, and the index for evaluating the stabilizing ability, and the index calculation unit refers to the index data according to a calculation result by the stability calculation unit and calculates the index for evaluating the stabilizing ability in the index calculation step.

16. The stability evaluation method according to claim 13, wherein the index calculation unit sets, as the reference value, a value selected from an average value, a maximum value, a minimum value, or an arbitrary representative value within the predetermined period based on a setting operation by an operator in the index calculation step.

17. The stability evaluation method according to claim 13, further comprising:

a cycle extraction step, by a cycle extraction unit, of extracting cyclical motion of each of the plurality of body motion sensors based on the body motion data accumulated in the body-motion recording unit; and a stability calculation step, by a stability calculation unit, of calculating, as a stable reference value, an average value of a parameter related to the cyclical motion extracted by the cycle extraction unit over a predetermined period and calculating, based on an amount of deviation from the stable reference value, a stable period during which a stable state of the cyclical motion is continued, wherein the index calculation unit refers to index data holding a correlation between the stable period calculated in the stability calculation step, the amount of deviation after the stable period, and the index for evaluating the stabilizing ability according to a calculation result by the stability calculation unit and calculates the index for evaluating the stabilizing ability in the index calculation step.

18. The stability evaluation method according to claim 13, wherein the index data holds a correlation between body motion of the wearer during competition and an incidence of injuries or failures during the competition.

* * * * *